United States Patent [19]
Wulff et al.

[11] Patent Number: 5,962,399
[45] Date of Patent: *Oct. 5, 1999

[54] PREPARATION OF ALKYLPOLYGLYCOSIDES AND CLEANING COMPOSITIONS COMPRISING SAME

[75] Inventors: Harald P. Wulff, Bryn Mawr; Paul A. Siracusa, Perkasie, both of Pa.; Patricia E. Bator, Secaucus; Barry A. Salka, Fair Lawn, both of N.J.; Michael W. Counts, Ambler, Pa.; Robert A. Aleksejczyk, Hatfield, Pa.; Patrick M. McCurry, Jr., Lansdale, Pa.; Robert S. McDaniel, Chalfont, Pa.; William G. Kozak, Hatfield, Pa.; Allen D. Urfer, Lansdale, Pa.; Gail Howell, Fort Mill, S.C.

[73] Assignee: Henkel Corporation, Gulph Mills, Pa.

[ * ] Notice: This patent is subject to a terminal disclaimer.

[21] Appl. No.: 08/969,254

[22] Filed: Nov. 13, 1997

Related U.S. Application Data

[62] Division of application No. 08/458,391, Jun. 1, 1995, Pat. No. 5,859,218, which is a division of application No. 07/957,333, Oct. 6, 1992, Pat. No. 5,449,763, which is a continuation-in-part of application No. 07/810,588, Dec. 19, 1991, Pat. No. 5,266,690, and a continuation-in-part of application No. 07/774,430, Oct. 10, 1991, abandoned, and application No. 07/876,987, Apr. 30, 1992, abandoned.

[51] Int. Cl.$^6$ .............................. C11D 3/22; C07G 3/00; C07H 1/00; C08B 37/00

[52] U.S. Cl. ............................ 510/470; 510/276; 510/535; 536/4.1; 536/18.6; 536/120; 536/124; 536/127

[58] Field of Search ..................... 510/470, 535; 252/FOR 239; 536/4.1, 18.6, 120, 124, 127

[56] References Cited

U.S. PATENT DOCUMENTS

| | | | |
|---|---|---|---|
| 3,547,828 | 12/1970 | Mansfield et al. | 252/351 |
| 5,266,690 | 11/1993 | McCurry, Jr. et al. | 536/18.6 |
| 5,370,816 | 12/1994 | Balzer et al. | 510/340 |
| 5,449,763 | 9/1995 | Wulff et al. | 536/18.6 |
| 5,734,029 | 3/1998 | Wulff et al. | 536/4.1 |
| 5,859,218 | 1/1999 | Wulff et al. | 536/18.6 |

*Primary Examiner*—Ardith Hertzog
*Attorney, Agent, or Firm*—Ernest G. Szoke; Wayne C. Jaeschke; Patrick J. Span

[57] ABSTRACT

A process for preparing high detergency or surfactant alkyl polyglycoside compositions and a purified alkyl monoglycoside and to compositions employing the polyglycosides for various end use applications. The process involves removal of a substantial portion of the monoglycoside present in a reaction product mixture containing alkyl polyglycosides resulting from the reaction of an alcohol and saccharide at elevated temperatures in the presence of an acid catalyst. Separation of the monoglycoside from the reaction product mixture may be carried out by molecular distillation.

33 Claims, 3 Drawing Sheets

PREPARATION OF ALKYLPOLYGLYCOSIDES AND CLEANING COMPOSITIONS COMPRISING SAME

This application is a divisional application of Ser. No. 08/458,391 filed Jun. 1, 1995, now U.S. Pat. No. 5,859,218, which is in turn a divisional application of Ser. No. 957,333, filed Oct. 6, 1992, issued as U.S. Pat. No. 5,449,763, which is in turn a continuation in part application of (i) Ser. No. 07/810,588 filed Dec. 19, 1991, now U.S. Pat. No. 5,266,690;

(ii) Ser. No. 07/774,430 filed Oct. 10, 1991, now abandoned; and (iii) Ser. No. 07/876,987 filed Apr. 30, 1992, now abandoned.

BACKGROUND OF THE INVENTION

1. Field of the Invention

This invention relates to a process for preparing high-detergency alkylpolyglycoside compositions and a purified alkyl monoglycoside and to compositions employing the alkylpolyglycosides for various end-use applications. In particular, the invention, involves removal or separation of a substantial portion of the alkyl monoglycoside present in a reaction product mixture containing alkyl polyglycosides resulting from the reaction of an alcohol and a saccharide at elevated temperatures in the presence of an acid catalyst. This invention further relates to the preparation of novel alkylpolyglycoside compositions having unexpectedly enhanced surfactant properties from readily available mixtures of alkylpolyglycosides of differing alkyl chain lengths, varying degrees of polymerization (DP) and surfactant properties. This invention further relates to the preparation of novel, economical and environmentally friendly mixtures of alkylpolyglycosides of preselected average alkyl chain length, and controlled average DP, for a wide variety of surfactant uses in personal care, cosmetic, detergent, as well as other household and industrial uses.

2. Statement of Related Art

The reaction of a reducing saccharide, e.g. an aldose or ketose saccharide, or a source thereof, with an alcohol results in the formation of a glycoside. Acids catalyze the reaction between a reducing saccharide and an alcohol. When the alcohol is an alkanol, the resulting glycoside is commonly referred to as an alkyl glycoside. Alkyl glycosides are structurally stable to alkali. Long chain, higher, alkyl ($C_{8-18}$) groups contribute to surface activity, e.g. detergency, of the glycoside. Thus, long chain alkyl monoglycosides and mixtures thereof with long chain alkyl polyglycosides are known materials, are known to be surface active in character and are known to be useful in a wide variety of household and industrial applications. It is also known that glycoside surfactants can be prepared by reacting a long chain alcohol with a saccharide reactant (e.g., a monosaccharide or a material hydrolyzable to a monosaccharide) at an elevated temperature in the presence of an acid catalyst. U.S. Pat. No. 4,987,225 contains an extensive listing of processes for preparing alkyl glycoside compositions. As disclosed therein, processes for preparing alkyl glycoside compositions are disclosed in U.S. Pat. No. 3,219,656 to Boettner (issued Nov. 23, 1965); U.S. Pat. No. 3,547,828 to Mansfield et al. (issued Dec. 15, 1970); U.S. Pat. No. 3,598,865 to Lew (issued Aug. 10, 1971); U.S. Pat. No. 3,707,535 to Lew (issued Dec. 26, 1972); U.S. Pat. No. 3,772,269 to Lew (issued Nov. 13, 1973); U.S. Pat. No. 3,839,318 to Mansfield (issued Oct. 1, 1974); U.S. Pat. No. 4,349,669 to Klahr (issued Sep. 14, 1982); U.S. Pat. No. 4,393,203 to Mao et al. (issued Jul. 12, 1983); U.S. Pat. No. 4,472,170 to Hellyer (issued Sep. 18, 1984); U.S. Pat. No. 4,483,979 to Mao (issued Nov. 20, 1984); U.S. Pat. No. 4,510,306 to Langdon (issued Apr. 9, 1985); U.S. Pat. No. 4,597,770 to Forand et al. (issued Jul. 1, 1986); U.S. Pat. No. 4,704,453 to Lorenz et al. (issued Nov. 3, 1987); U.S. Pat. No. 4,713,447 to Letton (issued Dec. 15, 1987); published European Application No. 83302002.7 (EPO Publication No. 0092355; Vander Burgh et al; published Oct. 26, 1983); published European Application No. 83200771.0 (EPO Publication No. 0096917; Farris; published Dec. 28, 1983); and published European Application No. 84303874.6 (EPO Publication 0132043; published Jan. 23, 1985).

During the course of the aforementioned acid-catalyzed saccharide reactant/long chain alcohol reaction process there is usually employed a substantial stoichiometric excess of the long chain alcohol reactant. The resulting reaction product mixture as initially made (i.e., without any intervening separation, fractionation or purification operations) typically contains a substantial molar excess of residual unreacted long chain alcohol, the monoglycoside of the long chain alcohol as the predominant glycoside molecular species both a mole and weight percentage bases, and the various higher degree of polymerization long chain alcohol polyglycoside species in progressively decreasing percentage amounts or proportions.

In accordance with the various prior art references, it has been conventional practice to remove the residual unreacted long chain alcohol from the indicated reaction mixture via various techniques such as vacuum distillation, organic solvent (e.g. acetone) extraction or fractionation, and thin (or wiped) film evaporation.

In commercial practice, depending on process economics and the properties of the desired alkylpolyglycoside product, a variety of fatty alcohol reactants may be selected for the reaction. These alcohols include mono alcohols, i.e., those having primarily a single alkyl chain, binary alcohol mixtures, i.e., having primarily two different alkyl chains of different carbon chain lengths, and even ternary mixtures. Binary mixtures of alcohols are available commercially from natural sources as well as synthetic techniques and are employed commercially for the production of the corresponding mixtures of alkylpolyglycosides. Especially important binary alcohol mixtures include the $C_8$–$C_{10}$, $C_{10}$–$C_{12}$, $C_{12}$–$C_{14}$, and $C_{16}$–$C_{18}$ where the alkyl groups are derived from naturally occurring fats and oils. Important ternary mixtures include the $C_{12}$–$C_{14}$–$C_{16}$ or $C_{10}$–$C_{12}$–$C_{14}$ alcohols. The oxo alcohol technology is also employed which provides mixtures containing an odd number of carbon atoms in the alkyl chain, for example an oxo alcohol composed of a mixture of $C_9$, $C_{10}$ and $C_{11}$ alcohols or $C_{12}$ and $C_{13}$ as well. Other synthetic alcohols may be provided by Ziegler Chemistry in which ethylene is added to a triethylaluminum, which is then oxidized to an alkoxide, which is subsequently converted to a mixture of linear alcohols.

Several methods of removal of the alcohols from the crude alkylpolyglycoside reaction product have been proposed. In Japanese Application No. 63-256398, laid open Apr. 16, 1990, No. 02-103202, a method of removing the alcohol by supercritical gas extraction, more specifically carbon dioxide, is described. In German Application DE 3932173, a two-stage distillation separation of alcohol from the mixture of alkyl glycosides is described using a falling film evaporator and thin film evaporator. Another distillation separation of alkyl glycosides and alcohol is described in U.S. Pat. No. 4,889,925 in which a viscosity-reducing agent is added to the alcohol-glycoside reaction mixture, which is then distilled at a temperature up to about 160° C. at a pressure of about 1 to $10^{-3}$ mbar.

If the long chain (fatty) alcohol is removed from the reaction mixture by one of the distillation or evaporation methods, the polysaccharide by-products and any other materials with low volatility remain in the alkyl glycoside product. Thus, in each of the methods described above the intent is to remove the alcohol leaving behind the alkyl glycosides, including the alkyl monoglycoside. The product will contain the monoglycoside of the long chain alcohol as the predominant glycoside species on a percentage basis and various higher degree of polymerization long chain alcohol polyglycoside species in progressively decreasing mole percentage amounts or proportions from the DP2 through DP10 and higher glycosides.

APPLICATIONS OR USE BACKGROUND

Since the practice of commercial scale processes for the production of alkylpolyglycoside products is governed chiefly by economic factors, it is not economically feasible to produce a wide variety of alkylpolyglycoside products for distribution in commerce. This is unfortunate since the applications or end use of these compositions is highly dependent on combinations of factors including carbon chain length, degree of polymerization, and additional factors such as the co-presence of impurities or minor amounts of residual surfactants. A wide variety of applications of alkylpolyglycoside products is known in the prior art. Illustrations of such uses include hard surface cleaner compositions, U.S. Pat. Nos. 4,606,850, 4,627,931; polymerization aids, U.S. Pat. No. 4,657,999; liquid soaps and bubble baths, U.S. Pat. No. 4,668,422; carpet shampoo and cleaning uses, U.S. Pat. No. 4,678,595; corrosion inhibitors, U.S. Pat. No. 4,705,665; dishwashing detergents, U.S. Pat. No. 4,732,704; viscosity modifiers, U.S. Pat. No. 4,732,696; potentiating agents, U.S. Pat. No. 4,748,158; contact lens cleaning, U.S. Pat. No. 4,767,559; detergent and shampoos, U.S. Pat. Nos. 4,780,234, 4,565,647, 4,663,069, 4,483,779, 4,396,520, 4,599,188, 4,493,773, 4,536,319, 4,154,706, 4,304,679; and cosmetics, U.S. Pat. Nos. 4,323,468, 4,196, 201. This list is not intended to be all inclusive but merely to illustrate the wide variety of applications and end uses of alkylpolyglycoside compositions requiring specialized formulation considerations, which for the most part must be determined empirically.

Donald E. Koeltzow and Allen D. Urfer, in a paper, "Preparation and Properties of Pure Alkyl Glucosides, Maltosides and Maltotriosides", JAOCS, Vol. 61, No. 10, pp. 1651–1655, October, 1984, examine various physical and functional properties of relatively pure alkyl glycosides having from 4 to 18 carbon atoms. This paper in turn refers to other publications dealing with synthesis of alkyl glucosides and an article by Francis A. Hughes and Baak W. Lew, reports on the physical and functional properties which render them suitable for use on biodegradable, surfactants, emulsifiers and detergents, "Physical and Functional Properties of Some Higher Alkyl Polyglucosides", JAOCS, Vol. 47, pp. 162–167, 1970.

U.S. Pat. No. 4,668,422, noted earlier, dealing with liquid soaps and bubble baths, prepared formulations in examples 6, 7 and 11 in which mixtures of two different alkylpolyglycosides were mixed in substantially equal amounts by weight, a $C_{9-11}$ alkylpolyglycoside having a DP of 1.3 and a $C_{12-13}$ alkylpolyglycoside having a DP of 2.8. At this substantially equal weight mixture no improvement is shown for examples 6, 7, or 11 over examples 1, 2, or 12 employing only one of the alkylpolyglycosides.

Similarly, in German Application DE 4 005 959, directed to liquid, foaming, cleaning agents, more specifically dishwashing detergents, an approach is taken whereby the mean degree of glycosidation (glycoside units per fatty alcohol residue) is not too high. The degree of glycosidation is controlled or determined by mixing two different alkylglycosides of differing alkyl lengths and differing degrees of glycosidation, in which each alkylpolyglycoside has an alkyl group of only one chain length, i.e. all $C_{10}$ and all $C_{11}$, or two different alkylpolyglycosides of mixed alkyl groups, i.e. $C_{8-10}$ and $C_{11-18}$, in which 1–10 parts of the $C_{11-18}$ is mixed with 1 part of $C_{8-10}$. Specifically shown are mixtures of $C_8C_{10}G_{1.8}$ with a $C_{12}C_{14}G_{1.2}$ or $C_{12}C_{13}G_{1.1}$.

More recently, however, Japanese Patent Application No. 63-298821 filed 25 Nov. 1988 and laid open Jun. 5, 1990 (Kokai No. 145696/90) describes a higher alkylglycoside composition said to possess foaming characteristics equivalent to general purpose anionic surfactants, such as sodium dodecylbenzene sulfonate and sodium polyoxyethylene (3EO) dodecyl sulfate. The formulated compositions are described as a mixture of individual or pure higher alkylglycosides characterized in an essential component of at least 14% by weight of component (A) a decyl or/and (B) an undecyl polyglycoside with at least 14% by weight of component (C) a dodecyl or/and (D) a tridecyl polyglycoside in which (A) has an average degree of polymerization (DP) of 1.1 to about 4.1; (B) has an average DP of 1.4 to about 2.5; (C) has an average DP of 2.4 to about 3.8 and (D) has an average DP of 2.9 to about 4.6. Both the number of alkyl carbon atoms and the DP are described as (5) essential, particularly for component (A). Compositions are described comprising 28–92% by weight of (A) with the remainder being alkylglycosides having non-essential alkyl glycosides having alkyl groups of 11–14 and higher. Described are:

(1) mixtures of (A) with (i) n-hexadecylglycoside or (ii) n-tetradecylglycoside (as non-essential components);

(2) a mixture of (A) with a dodecylglycloside having a DP of 1.8, outside the DP range for component (C) above as a non-essential component; and (3) mixtures of one or two of essential components (A) through (D) above with one non-essential component (either an alkyl group other than 10–13 carbon atoms or a DP outside the range for the essential components).

While the approach of the Japanese reference to mix glycosides of individual, single, alkyl groups could allow simulation of foaming surfactant properties, unfortunately, the use of mixtures of alkylpolyglycosides derived from readily available binary mixtures of fatty alcohols as described above are not encompassed within the teachings of the Japanese reference. The mixtures of alkylpolyglycosides derived from mono or relatively pure cut alcohols suggest a completely different approach than the unique, surprising and economically practicable approach hereinafter described with reference to the present invention.

In another approach, European Patent Application, EP 92355, published Oct. 26, 1983, describes the preparation of fatty glycoside mixtures by reaction of a saccharide-containing composition of the formula A-O-(G)$_x$, where A is hydrogen or an organo group of less than 8 carbon atoms, G is a saccharide and x is an integer of at least 1, with a lipophilic alcohol having at least 8 carbon atoms and a surfactant additive of the formula R$_f$O(G)$_n$, where R$_f$ is a lipophilic organo group having at least 8 carbon atoms, G is a saccharide unit and n is an integer of at least 1. The reaction may be controlled to promote fatty glycoside mixtures of varying degrees of glycosidation. The applicants indicate generally that the mixture may be fractionated into divergent fatty glycoside fractions of differing HLB values, which may be recombined to make a fatty glycoside mixture of predetermined HLB values. No specific example of such a mixture is given. This approach, using individual divergent fractions, is similar to the Japanese approach of combining glycosides of individual, single, alkyl groups.

While these mixtures of monoglycosides and higher polyglycosides have properties permitting their function as detergents and surfactants, they have been typically formulated in the past with other anionic, nonionic or cationic surfactants to provide for enhanced surfactant properties, since standing alone they fell short of properties achieved by other surfactants, such as the ethoxylated surfactants.

SUMMARY OF THE INVENTION

It has now been discovered that an alkyl polyglycoside product having improved properties, particularly detergent or surfactant properties may be provided by removing a substantial portion of the alkyl monoglycoside (as will be described in more detail hereinafter). By removal of the portion of alkyl monoglycoside as described by the method of the present invention, the distribution of the alkylpolyglycosides present in the mixture is changed which results in improved performance. Thus, the method of the present invention provides a means for changing the distribution of the polyglycoside fractions in the alkylpolyglycoside product resulting in improved properties. As indicated earlier, end-use applications are dependent not only on carbon chain length but also on degree of polymerization. The present invention provides a means for adjusting the average degree of polymerization, thus controlling the hydrophilic portion of the alkyl polyglycoside molecule to provide optimum or maximum hydrophilic-lipophilic balance (HLB) for the particular end-use application under consideration. There can, accordingly, be provided alkylpolyglycoside products having maximum stand-alone surfactant properties, thus requiring minimal, if any, formulations with other surfactants, as typically required in the past.

The present invention also results in providing a purified alkyl monoglycoside product (the removed monoglycoside) which may be employed in applications where monoglycosides find utility or for conversion to other derivatives. Thus, the present invention unexpectedly provides a two-fold benefit, (a) an improved alkylpolyglycoside product and (b) a purified alkyl monoglycoside product. The properties of the alkylpolyglycoside product having the changed distribution of polyglycoside fractions can be further modified and enhanced by preparing alkylpolyglycoside compositions thereof having preselected or predetermined average alkyl chain length, primarily from binary or ternary mixtures of the alkylpolyglycosides. The alkylpolyglycoside products of changed distribution may also be modified by the addition of amounts of purified alkyl monoglycoside removed from another alkylpolyglycoside of a different alkyl chain length i.e., a purified monoglycoside of a $C_8$–$C_{10}$ added to a changed distribution $C_{12}$–$C_{14}$ alkylpolyglycoside.

In addition, in removing the monoglycoside, residual alcohol which may remain in small amounts in the product after the removal of alcohol following completion of the reaction, is further removed along with the removed monoglycoside. Such alcohol may then be further processed to remove it from the monoglycoside and then recycled to the reaction stage, thereby providing a further economic benefit.

The foregoing is a brief summary of the present invention and advantages thereof, which will be presented and illustrated in more detail below.

DETAILED DESCRIPTION OF THE INVENTION

Other than in the operating examples, or where otherwise indicated, all numbers expressing quantities of ingredients or reaction conditions used herein are to be understood as modified in all instances by the term "about".

It is an object of this invention to provide alkyl polyglycoside compositions having a combination of physical and functional properties desired for use in a wide variety of end uses, including cosmetic, personal care and cleaning applications. It is a further, more specific object, to enable the preparation of alkyl polyglycoside compositions having maximum stand-alone surfactant properties for specific end-use applications resulting from control of the average degree of polymerization and thereby the HLB of the composition.

It is also a further object to provide a concentrated, substantially pure alkyl monoglycoside composition, essentially free of alkyl polyglycoside fractions, by separating the alkyl monoglycoside fraction from the mixture of mono and polyglycosides resulting from the reaction of an alcohol having from about 6 to about 20 carbon atoms and a saccharide in the presence of an acid catalyst.

Figure 2A:
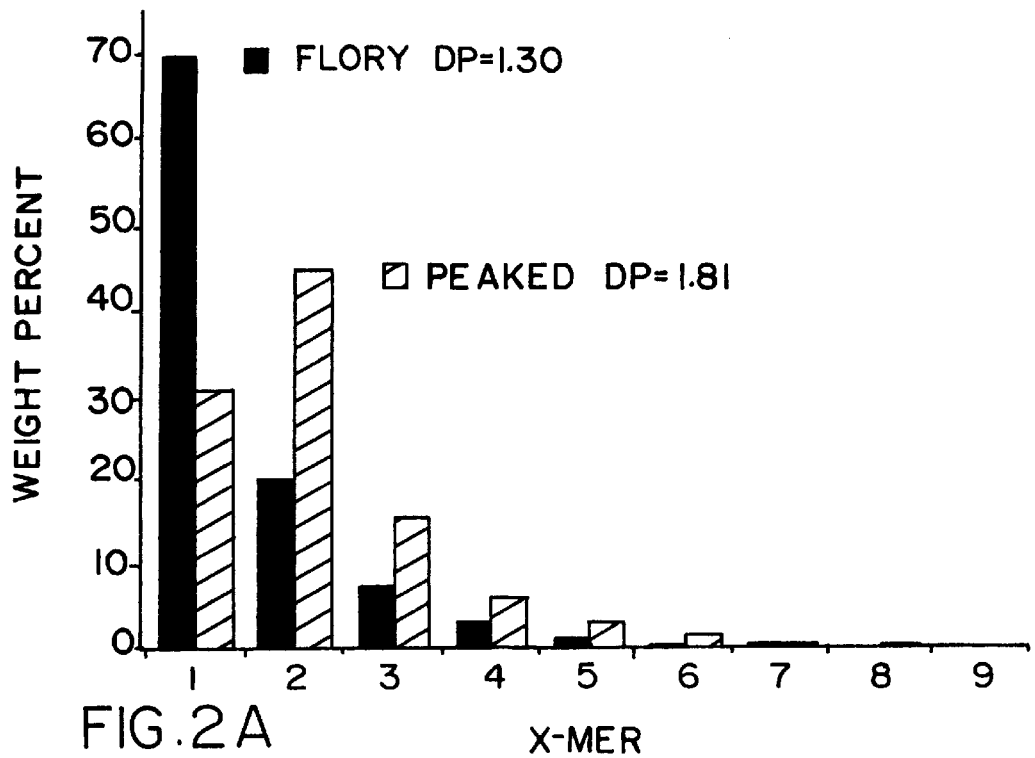
FIGS. 2A and 2B are bar graph representations of the reaction product before the use of the present invention and after use of the present invention. The solid bars show a typical Flory distribution of oligomer (x-mer) fractions in the reaction product having an average Flory DP in FIG. 2A of 1.3 and an average Flory DP in FIG. 2B of 1.70. The hatched bars show a "peaked" distribution after practice of the present invention having an average peaked DP of 1.81 in FIG. 2A and an average peaked DP of 2.14 in FIG. 2B, after removal of about 80% and 60% of the monoglycoside respectively in FIGS. 2A and 2B.
Figure 2B:
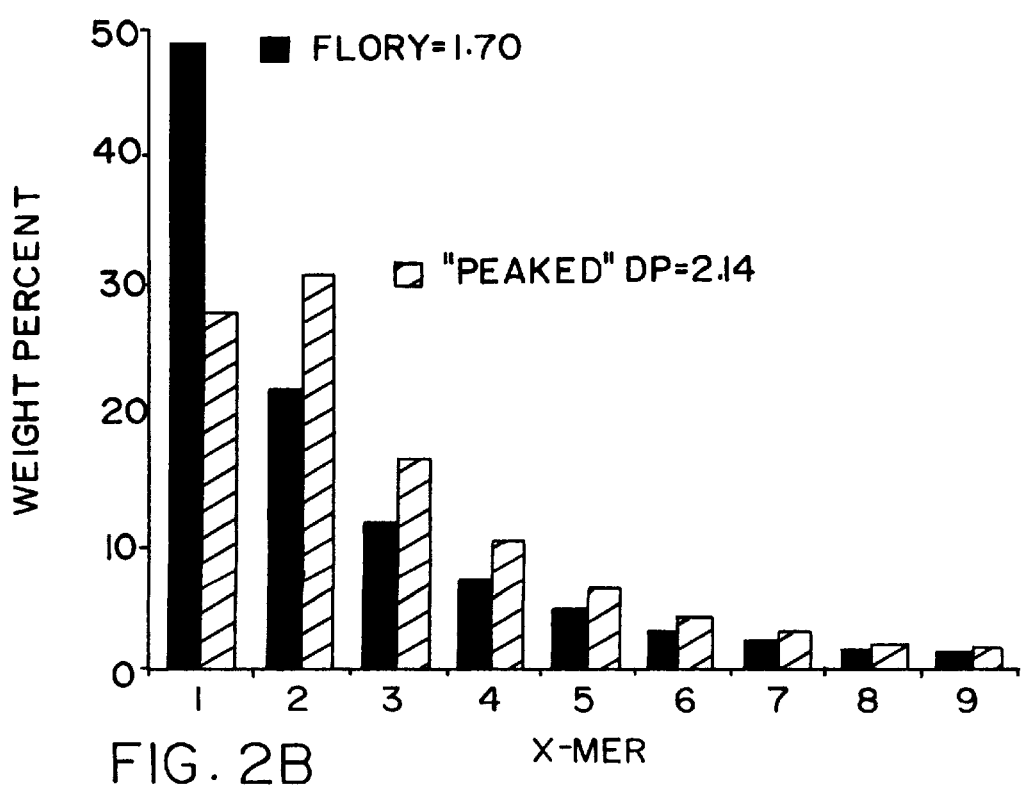
Figure 2C:
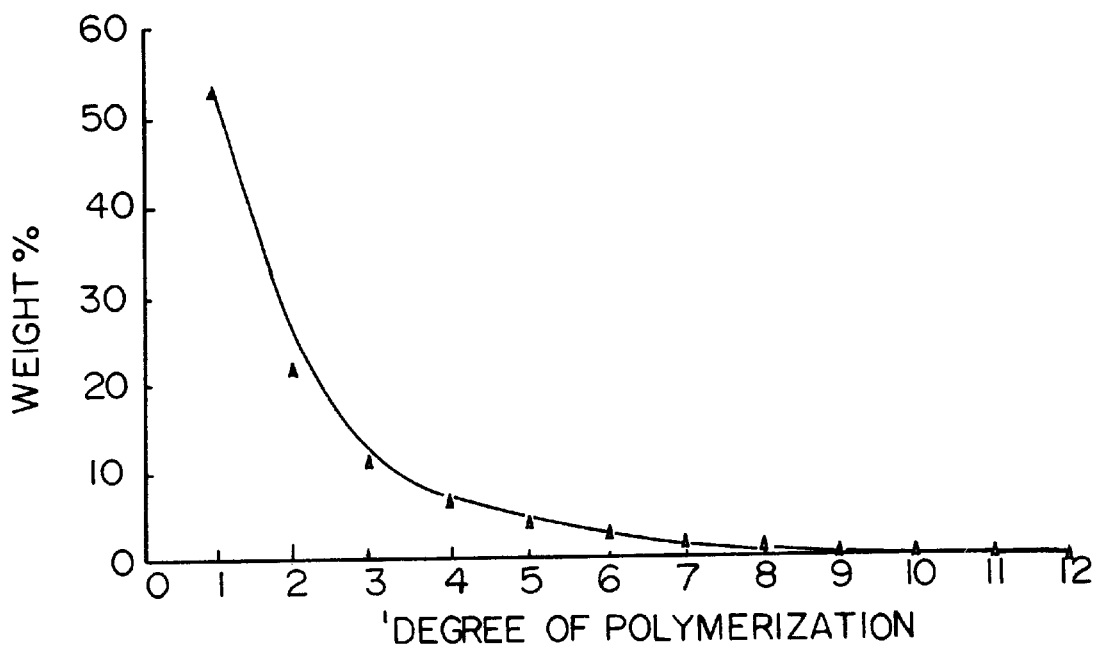
FIG. 2C is another representation of the typical Flory distribution, in another form of graph, in which the designated points which the curve joins indicate the amounts of DP 2, DP 3 and higher, DP 4 through DP 12.

As described in the related art section above, the initial reaction product of the alcohol and saccharide in the presence of an acid catalyst results in a mixture of a monoglycoside of the alcohol and various higher degrees of polymerization (DP) polyglycosides in progressively decreasing amounts, i.e., the diglycoside (DP2), the triglycoside (DP3) and the higher polyglycosides (DP4 and higher). A typical distribution of the various oligomers provided is a Flory distribution, examples of which are seen in the solid bars of FIGS. 2A and 2B and the curve in FIG. 2C. While the specific distribution of the various fractions may vary somewhat for various reaction products, the overall distribution curve seen in the solid bars in FIGS. 2A and 2B is the same, though the average DP of the reaction mixture may vary due to the differing distribution of the various fractions, i.e., DP1, DP2, DP3 and higher fractions. Typically, the Flory distribution of the reaction product after removal of the excess alcohol will have an average degree of polymerization above 1.2, i.e., about 1.4, with a monoglycoside content in the range of about 50–70% by weight of the glycoside product. Commercially available products typically have an average Flory DP of about 1.3–1.7.

As indicated earlier by use of the method of the present invention, the distribution of the alkyl polyglycosides present in the mixture is changed resulting in a product having a peak at the DP2 and the average DP of the resulting product is higher than the average DP of the initial reaction product before removal of a portion of the monoglycoside, preferably at least about 0.2 units higher. In the past, attempts to provide an increased average DP involved control of the amounts of alcohol and saccharide and the reaction conditions, particularly temperature and time, and the nature and amount of catalyst. Rather than increasing the DP2 oligomer, such attempts resulted in either increased amounts of the higher DP oligomers, which do not result in improved surfactant or detergent properties, or resulted in increased degradation products or undesirable by-products. By means of the present invention, a "peaked" product having a distribution peak at the DP2 oligomer and a higher average DP, results, which has improved surfactant and detergent properties.

As indicated in the summary above, these peaked products may be further enhanced by mixing peaked products of varying or different alkyl chain lengths to provide a composition having a preselected or predetermined average alkyl chain length, preferably by mixing binary or ternary mixtures of the peaked alkylpolyglycosides, as described in commonly assigned co-pending applications, U.S. Ser. Nos. 07/774,430 and 07/876,967 noted earlier. In these co-pending applications, compositions of at least binary mixtures of typical Flory distribution products, are described, which provided unexpected improvement in properties. It has also been discovered that mixtures of the peaked products (non-Flory distribution) of the present invention results in further enhancement or improvement of at least some of the properties of the composition, over those of similar mixtures of typical Flory distribution. It has also been found that enhanced properties of the individual peaked products may be obtained by adding them to purified monoglycoside having a different alkyl chain length from that of the peaked product.

The glycoside products of the reaction of an alcohol and saccharide may be represented by the formula

wherein R is a residue of an alcohol, 0 is oxygen, G is a glycoside residue, and x is the average degree of polymerization (DP) resulting from weighting of the various mono-, di-, tri- and higher glycoside fractions present in the product and is a number of from about one to about three.

The average degree of polymerization is thus defined as the ratio of saccharide rings to the R groups in the alkyl glycoside. The monoglycoside fraction would have one saccharide ring, the diglycoside would have 2, the triglycoside would have 3 with the higher glycoside having corresponding more rings, the average of which in the currently available commercial product therefore being typically greater than about 1, generally in the order of about 1.2 to about 1.7, with preferred mixtures at about 1.3 to about 1.7.

The alkyl polyglycoside products represented by the formula above contain a lipophilic group, the R group, and a hydrophilic group, the $OG_x$ group. For detergent or surfactant-use application, the product should have a hydrophilic-lipophilic balance (HLB) of from about 10 to about 16, and preferably about 11 to about 14. The HLB value of a product may be calculated by the formula $$HLB = \frac{([MW_{AGU}] \times DP + MW_O)}{(([MW_{AGU}] \times DP + MW_O) + MW_R)} \times 100/5$$

where AGU is typically the anhydro glucose unit in G having a molecular weight of 162, $MW_R$ is the molecular weight of the lipophilic group R, $MW_O$ is 16, the molecular weight of oxygen, and DP is the average degree of polymerization as predicted by Flory's statistical treatment. The present invention provides a method for the preparation of alkyl polyglycoside compositions having a desirable HLB for detergent or surfactant use application with the specific R groups of the alcohols employed in the reaction.

The lipophilic R groups in the alkyl polyglycosides are derived from alcohols, preferably monohydric, for the detergent, surfactant-use applications and should contain from about 8 to about 20, preferably about 9 to about 18 carbon atoms, with an average of about 10 to about 13 being most preferred, to provide R groups of sufficient length for detergent, surfactant-use applications. While the preferred R groups are saturated aliphatic or alkyl, there may be present some unsaturated aliphatic hydrocarbon groups. Thus, the preferred groups are derived from the fatty alcohols derived from the naturally-occurring fats and oils, such as octyl, decyl, dodecyl, tetradecyl, hexadecyl, octadecyl, oleyl and linoleyl, but R groups may be derived from synthetically produced Ziegler alcohols or oxo alcohols containing 9, 10, 11, 12, 13, 14 or 15 carbon atoms. The alcohols of naturally-occurring fatty acids typically contain an even number of carbon atoms and mixtures of alcohols are commercially available such as mixtures of $C_8$ and $C_{10}$, $C_{12}$ and $C_{14}$, and the like. Synthetically-produced alcohols, for example those produced by an oxo process contain both an odd and even number of carbon atoms such as the $C_9$, $C_{10}$, $C_{11}$ mixtures, which are also available commercially.

Saccharide reactants which can be employed to prepare the aforementioned glycoside surfactants include reducing monosaccharide materials containing 5 or 6 carbon atoms such as, for example, glucose, galactose, mannose, xylose, arabinose, fructose, etc. as well as materials which are hydrolyzable to form monosaccharides such as lower alkyl glycosides (e.g. methyl glycoside, ethyl glycoside, propyl glycoside, butyl glycoside, etc.), oligosaccharides (e.g. sucrose, maltose, maltotriose, lactose, zylobiose, melibiose, cellobiose, raffinose, stachyose, etc.) and other polysaccharides. Such saccharide reactants may be employed in dry (e.g. anhydrous) form or, if desired, may be employed in the form of hydrated solids or aqueous solutions thereof. If utilized in the form of a solution, it is preferred that the resulting reaction mixture contain only small amounts of water, i.e., less than about 1% by weight, preferably less than about 0.5% i.e. less than 0.25 or 0.1%.

While the preparation of the initial alkyl glycosides reaction mixture employed in the present invention forms no part of the present invention, a brief description generally of the preparation follows. The molar ratio of alcohol to monosaccharide in the reaction mixture can vary widely but is typically between about 1.5:1 to about 10:1, and preferably between about 2.0:1 to about 6.0:1. The particular molar ratio chosen depends upon the desired average degree of polymerization (DP) of the monosaccharide reacted with the alcohol. Preferably, the ratio of alcohol to monosaccharide will be chosen to allow the production of an alkyl glycoside product having a DP between about 1.2 to about 1.7, and more preferably about 1.3 and about 1.6.

The reaction between the hydrophobic alcohol reactant and the saccharide reactant to form the glycoside surfactant is typically conducted at an elevated temperature and in the presence of an acid catalyst. As a general rule, said reaction is preferably conducted at a temperature of from about 80° to about 140° C., preferably about 90° to about 120° C., and at pressures (about 10 to about 100 mm Hg absolute), which facilitate water removal, while at the same time maintaining the desired reaction temperatures.

Acid catalysts suitable for use include strong mineral acids such as hydrochloric acid, sulfuric acid, nitric acid, phosphoric acid, hypophosphorous acid, etc.; strong organic acids such as para toluenesulfonic acid, methanesulfonic acid, trifluoromethanesulfonic acid, mono- or polyalkylated aryl mono- or polysulfonic acids such as dodecylbenzenesulfonic acid, etc.; and macroreticular acidic ion exchange resins such as macroreticular sulfonic acid ion exchange resins, perfluorinatedsulfonic acid resins, etc. Typically, said acid catalyst will be employed in an amount ranging from about 0.0005 to about 0.03 (preferably from about 0.002 to about 0.015) moles thereof per mole of saccharide used.

Typically, the above-described reaction process will be conducted over a reaction period of from about 1 to about 20 (preferably from about 2 to about 10) hours. Upon completion of the reaction, the acid catalyst is typically neutralized by an alkaline substance, preferably an alkali metal hydroxide such as sodium hydroxide, used in an amount about equal, on a stoichiometric basis, to the amount of material needed to neutralize the catalyst.

After neutralization of the acid catalyst, typically excess unreacted alcohol is removed. Alcohol removal is generally accomplished by evaporation, e.g. distillation, of the alcohol. The use of a wiped film evaporator is particularly convenient for this purpose, e.g. operated at about 160°–200° C. and about 0.1 to 3 mm Hg pressure. As indicated in the discussion of related art, other methods of removal of the alcohol may be employed including distillation techniques and supercritical extraction under conditions for removing alcohol to levels below about 5%, more desirably below about 2% by weight to about 0.5%.

At this point, the resulting commercial product, substantially devoid of alcohol, is typically a mixture of alkyl glycosides, in which for purposes of this invention the average alkyl group will contain from about 8 to about 20, preferably about 9 to about 18, most preferably an average of about 10 to about 13, carbon atoms, having the typical Flory distribution discussed earlier above.

In accordance with the present invention, the product is then treated under conditions which separate a highly concentrated monoglucoside stream from the mixture to provide a concentrated, purified alkyl monoglycoside and a polyglycoside product having improved detergent surfactant properties, containing the higher polyglycosides originally present in the mixture and a changed distribution or concentration of fractions due to the removal or separation therefrom of the monoglycoside. The changed distribution will vary dependent on the amount of monoglycoside separated from or removed from the original mixture.

A substantial portion of the monoglycoside will be removed or separated from the original reaction mixture. Preferably, at least about half of the monoglycoside content of the original reaction mixture will be separated therefrom. As indicated earlier, the typical Flory distribution of the reaction product after removal of the excess alcohol will have a monoglucoside content of about 50 to about 70% by weight. The polyglycoside content of the original reaction mixture will accordingly typically comprise about 50 to about 30% by weight. With removal of at least about half of the monoglycoside, the remaining mixture of alkyl polyglycosides and unremoved monoglycoside, will contain by weight at least about 45% of the polyglycosides having a DP of 2 and higher, and an average DP at least about 0.2 units higher than that of the original reaction mixture prior to removal of the monoglucoside. The remaining mixture will contain substantially all the polyglycosides present in the original reaction mixture prior to removal of the monoglycoside, particularly those having the higher DPs of DP4 and higher. Dependent on the particular specific method employed in separating the monoglycoside from the original reaction mixture, some small amounts of lower DP fractions, i.e. DP2 and DP3 fractions, may be removed along with the monoglucoside, particularly under conditions where large amounts of monoglucoside are removed from the reaction mixture. Preferably conditions are selected so that less than 10%, and more preferably less than 5%, of such polyglycoside fraction present in the original reaction mixture, will be removed along with the monoglycoside fraction removed. The monoglycoside fraction removed will accordingly be a concentrated, substantially pure product containing less than about 10%, more desirably less than about 5%, preferably less than 1% polyglycoside. By definition, a pure monoglycoside will have a degree of polymerization of 1 (DP1). With decreasingly smaller amounts of polyglycoside present, the concentrated, substantially pure alkyl monoglycoside product of this invention will accordingly approach a DP of 1, with the average DP being less than about 1.1, more desirably less than about 1.05 and preferably less than 1.02.

The separation of the monoglycoside from the original reaction mixture of alkyl monoglycoside and alkyl polyglycosides after removal of the alcohol, may be carried out by molecular distillation. Molecular distillation is a preferred method as it tends to be far more efficient and less expensive than other processes described in the prior art noted above, such as precipitation methods. Molecular distillation is accordingly preferred at the present time from a commercial operation viewpoint, and for purposes of this invention will be the method described in detail herein.

Figure 1:
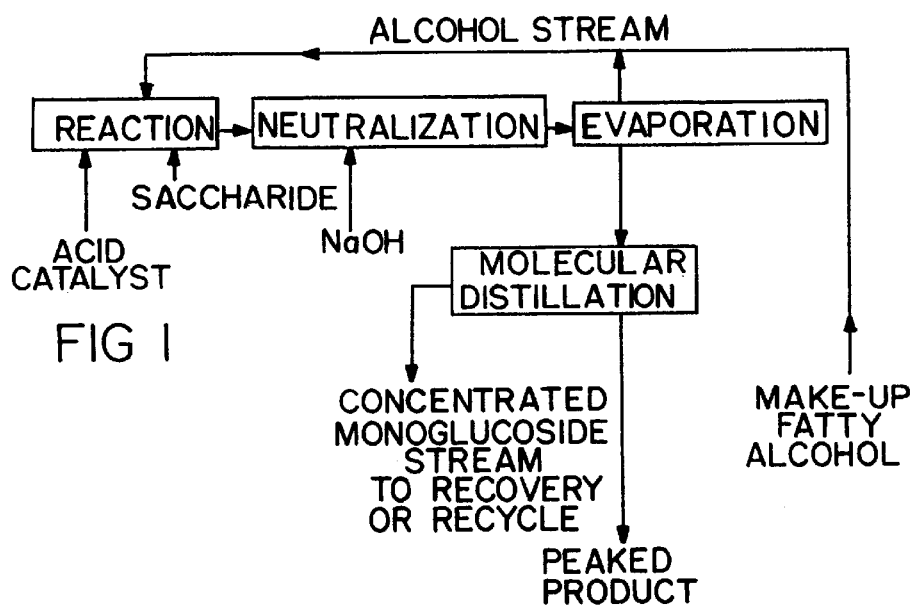
FIG. 1 is a block diagram of the process of preparation of the alkyl glycoside reaction product of an alcohol and a saccharide in the presence of an acid catalyst including the molecular distillation to provide the purified alkyl monoglycoside and improved detergency alkyl polyglycoside products of the present invention.

FIG. 1 of the drawing is a block diagram of a process of preparation of the alkyl glycoside reaction product of an alcohol and a saccharide in the presence of an acid catalyst, including an evaporation step and a molecular distillation step. As shown in FIG. 1, residual alcohol is removed and is typically recycled to the reactor.

Figure 3:
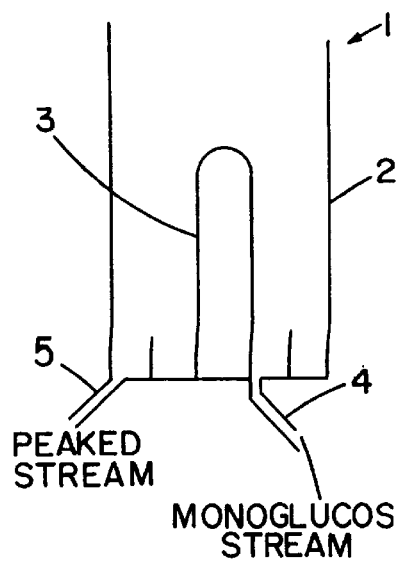
FIG. 3 is a diagram view of one molecular distillation still useful in the present invention with an internal condenser within the heated column.

FIG. 3 is a simplified, expanded, non-scale view of one molecular distillation still 1, useful in the present invention having an internal condenser 3, within the distillation heated chamber 2. The monoglycloside is withdrawn from the distillation chamber through passage 4, while the polyglycosides fractions now containing less monoglycoside is removed through conduit 5.

Referring again to FIG. 1, in the typical evaporation operation for removal of the excess alcohol, a temperature of about 170 to 200° C., preferably about 180 to about 200° C., is employed at pressures above 1 millibar. A molecular distillation as shown is operated at temperatures above 200° C., preferably above 230° and typically in the range of about 240 to about 250° C. By "molecular distillation" as used herein is meant short path, high vacuum distillation. On a laboratory scale, pressures of about 0.1 mbar and lower may be employed. On a commercial scale, pressures will desirably be in the range of 0.01 mbar and lower, preferably about 0.001 mbar or lower. In the molecular distillation, a very short distance is employed between the vaporization and condensing surfaces, which is as close as possible. In practice the actual gap is bounded by about 0.1 to about 10 times the mean free path of distilling molecules which is defined by kinetic theory. The residence time is as short as possible to minimize thermal degradation of the alkyl polyglycosides, less than about 2 minutes and preferably less than about 15 seconds.

Figure 4:
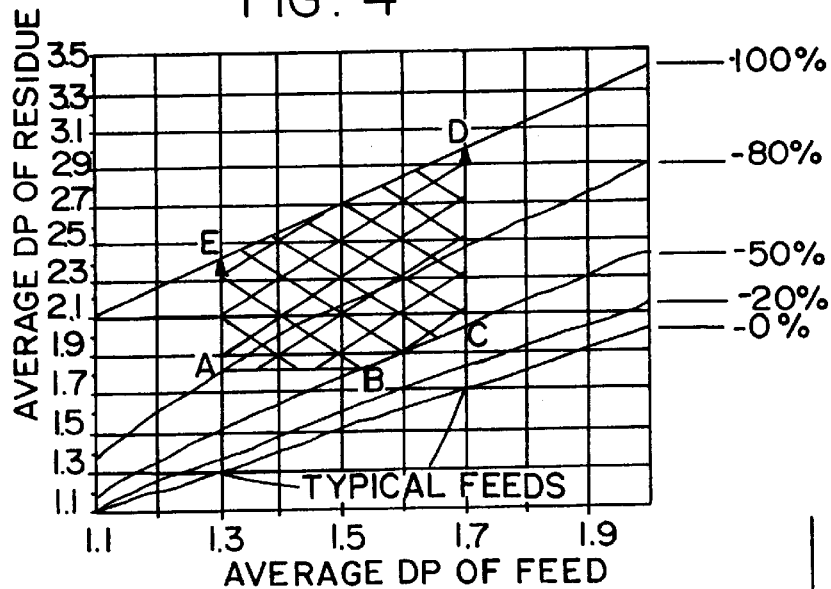
FIG. 4 is a graphical representation of the "peaked" versus the feed average DP at various percentages of initial monoglycosides removed and showing the preferred area ABCDE of the resulting alkyl polyglycoside products after use of the present invention from typical feeds having average DPs of about 1.3 and about 1.7.

As indicated earlier, the alkylpolyglycoside product after removal of monoglycoside will vary in its composition dependent on the amount of monoglycoside removed. In the molecular distillation process, if no polyglycoside is removed along with separation of the desired amount of monoglycoside, the resulting polyglycoside product will contain the polyglycosides present in the original mixture, along with any monoglycoside not separated from the original mixture. Thus, the relative distribution of the various components, mono- and poly-glycosides, in the resulting product changes, and the concentration in the product of the polyglycosides relative to the monoglycoside increases, as well as the concentration of individual polyglycosides to the total, i.e. DP2 and DP3 fractions in relation to the sum of all DP fractions. With the removal of monoglycoside the average DP of the resulting product is higher. FIG. 4 illustrates the average DP of preferred residue products of the present invention resulting from molecular distillation of typical feed having average DPs of about 1.3 to about 1.7. With removal of at least about 50% of the monoglucosides (-50% line), the preferred products of the present invention from such feeds will have an average DP of at least about 1.8 and about at least 0.2 units higher than the average DP of the initial feed and will fall within the trapezoidal area defined by ABCDE of FIG. 4. If the amount of monoglycoside separated from the original reaction mixtures is in a sufficient amount to provide that the monoglycoside retained in the resulting product is less than the total of DP2 and DP3 fractions, or more preferably, less than that of the DP2 fraction, it can be readily seen from FIGS. 2A and 2B illustrating Flory (solid bars) versus examples of "peaked" distributions (hatched bars), that the DP2 and DP3 distribution now illustrates a non-monoglycoside "peaked" distribution in the resulting products, which retain the DP4 and higher fractions in the resulting products prepared by molecular distillation.

The following examples serve to illustrate, but not limit, the invention. All parts and percentages are by weight, unless otherwise noted.

EXAMPLE 1

A crude reactor product from the reaction of a saccharide (glucose) and an alcohol (Lorol 1214A, an alcohol having a mixture of $C_{12}$, $C_{14}$ and $C_{16}$ alkyl groups in a weight ratio of 68, 26 and 6 respectively), in the presence of an acid catalyst was taken directly from a reactor. The reaction mixture at a concentration of about 26% dry solids (ds) was neutralized with 33 weight % sodium hydroxide using about 101% of theoretical amount of sodium hydroxide.

The neutralized reactor product was the concentrated to ca. 70% ds by vacuum distillation under "mild" conditions. This was accomplished in a Leybold Heraeus wiped film evaporator with external condenser at 2 mm Hg pressure, 105° C. feed temp., 160° C. evaporator body (wiped zone), 140° C. evaporator residue zone, 30–35° C. external condenser temp., and a feed rate of ca. 600 cc/hr. The resulting product with Flory distribution was typically 65–75 ds, and flows at 80° C.

A "peaked" alkylpolyglycoside surfactant was prepared from this 70 ds product by high vacuum molecular distillation using a Leybold Heraeus wiped film molecular still with an internal condenser. Typical distillation conditions were: 0.01 millibar (ca. 8 microns, measured between the pump and cold trap), 110° C. feed temperature, 240° C. evaporator body (wiped zone), 200° C. residue zone, 140° C. internal condenser, and a feed rate of ca. 350 cc/hr. The alkylpolyglycoside residue contained about 20 wt. % monoglucosides on an alkylpolyglycoside solids basis. To improve the color the recovered product was then bleached using 30% hydrogen peroxide to provide a product typical having about 18–21 Klett color (5% solution at 4 cm length).

EXAMPLE 2

This example serves to illustrate the distribution of the various fractions in the product before and after distillation as described in Example 1. In this instance, about 79.7% of the monoglycoside (50% of the total initial weight) was removed changing the Flory distribution of the starting material to that indicated below in Table 1.

TABLE 1

|  | STARTING weight % | 79.7% MONOS REMOVED weight % |
|---|---|---|
| DP 1 | 62.7 | 25.4 |
| DP 2 | 21.2 | 42.4 |
| DP 3 | 8.7 | 17.4 |
| DP 4 | 3.9 | 7.7 |
| DP 5 | 1.8 | 3.6 |
| DP 6 | 0.9 | 1.7 |
| DP 7 | 0.4 | 0.8 |
| DP 8 | 0.2 | 0.4 |
| HIGHER | 0.2 | 0.4 |
| AVERAGE DP | 1.4 | 2.0 |

EXAMPLE 3

Distillations were conducted to effect separation of monoglycosides on $C_{11}$, $C_{12}$ and $C_{14}$ feeds. The conditions of the distillation and results can be seen from the following Table 2 which includes a sample of the $C_{12}$–$C_{14}$ product of Example 1.

TABLE 2

| Feed | DP Feed | Temperature ° C. | Pressure mm | % DP 1 Removed | DP Residue |
|---|---|---|---|---|---|
| $C_{11}$ | 1.16 | 240 | 0.1 | 95 | 1.92 |
| $C_{12}$ | 1.39 | 242 | 0.1 | 80 | 1.97 |
| $C_{14}$ | 1.46 | 245 | .02 | 83 | 2.14 |
| $C_{12}$-$C_{14}$ (Example 1) | 1.38 | 240 | .008 | 83 | 2.01 |

As indicated initially above, the present invention results in a purified monoglycoside product stream which will find utility in applications where monoglycosides find utility or for conversion to other derivatives. It has also been discovered that the alkyl monoglucoside product removed as described above is useful as a starting feed material for preparing low mole ratios (e.g. 1.1 to 1.5 anhydroglucose groups per fatty group) alkyl polyglycoside products which may be prepared at high solids, above 40 weight/weight % in fatty alcohol. Thus, the alkyl monoglycosides isolated by molecular distillation, or the other methods described above, are mixed with the fatty alkyl (preferably $C_8$ and above) alcohol and heated in the presence of an acid catalyst, such as an alkylbenzene sulfonic acid to provide an alkyl polyglycoside with mole ratios of anhydroglucose to bound fatty groups of 1.5 or lower.

The acid catalysts are the same acid catalysts described earlier above in the preparation of the alkyl polyglycoside mixtures having the Flory distribution from which the monoglycoside forming the starting material herein has been removed. In a batch process the acid catalyst is employed in a level of about 1 to about 10 milliequivalents per mole of anhydroglucose, preferably at about 5 to about 8 milliequivalents. Similarly, the fatty alcohols are the same as noted earlier containing about 8 to about 20, preferably 9 to about 18, and most preferably about 10 to about 13, carbon atoms. The alcohol is employed in an amount to provide less than about 4 moles of alkyl groups per anhydroglucose unit, preferably about 1.5 to about 3 moles alkyl group per anhydroglucose unit. The temperature and pressures employed are also the same, about 90 to about 120° C. being preferred at pressures of about 10 to about 100 mm Hg absolute). Typically, about 100° C. is employed.

The polymerization reaction may be carried out in a batch or continuous process. In a continuous process, a monoglucoside fraction resulting from molecular distillation of an alkyl polyglycoside/fatty alcohol feed is continuously injected or fed with catalyst or alcohol/catalyst mixtures and passed through a heated zone. The residence time in the heated zone and the catalyst level are adjusted to give the desired product. In a desirable application of the present invention, the monoglucosides are continuously distilled and isolated together with the fatty alcohol, mixed with catalyst, and passed through a heated zone characterized by high temperatures and short residence time with sufficient vacuum to remove any water formed in the process. A wiped film evaporator is an example of a suitable piece of equipment for the reaction zone.

EXAMPLE 4

The use of the alkyl monoglycoside stream removed from the Flory distribution by molecular distillation, as described above, is illustrated by the following, in which a $C_{12}$ alkyl monoglycoside fraction and a $C_{12}$ alkanol were employed with 6 milliequivalents of LAS catalyst and 2.25 moles of fatty alkyl groups per anhydroglucose unit at about 60% dry solids by weight, at a temperature of 100° C. The results may be seen from Table 3 below:

TABLE 3

| COMPONENT | 0 Min | 60 Min | 120 Min | 180 Min |
| --- | --- | --- | --- | --- |
| % FOH | 43.32% | 45.78% | 46.28% | 48.17% |
| % MONOSACCAHARIDES | 1.17% | 1.05% | 1.11% | 0.87% |
| % DP1* | 99.0% | 77.0% | 69.8% | 66.3% |
| FLORY DP | 1.01 | 1.20 | 1.29 | 1.34 |

Compositions determined by TMS/GC with internal standard
*Alkyl glycoside basis.

The alkylpolyglycoside remaining after removal of monoglycoside by molecular distillation, or the other processes described, will result in a lower viscosity product where the products have less than about 40%, preferably less than about 35% by weight monoglycoside and an average DP of about 1.8 and above up to about 3.0, preferably about 1.8 to about 2.5. The preferred products will further contain less than 20% by weight of polyglycoside having a DP of 5 and higher. Such products retain the improved surface-active properties of the polyglycoside product resulting from the present invention, but the products afford lower solution viscosity and are then easier to handle and may be shipped with less water or cosolvent. This unexpected advantage also results in lower handling losses and provides for greater flexibility in formulating finished blended surfactant products in the various end-use applications in which the alkylpolyglycosides find utility, such as cleaning compositions, soaps, detergents, shampoos, personal care products and cosmetics. The products, accordingly, avoid the problems encountered in high viscosity solutions which are difficult to pump, blend and dilute and frequently result in loss of material due to difficulty in completely emptying storage vessels of product too viscous to flow readily. While cosolvents such as alcohols may be used to dilute highly viscous products, such dilution with alcohols and/or water result in higher shipping costs per pound of active product. Further alcohols or other cosolvents may result in adverse flammability characteristics and their presence may cause difficulty in formulating a finished product blend in which such cosolvents are undesirable. The products of the present invention overcome such problems. The foregoing can be demonstrated by the following Example 5.

EXAMPLE 5

In this example, the Brookfield viscosity in centipoise (cps) at 25° C. was measured of 10% solids solution in water of polyglycosides from $C_{12}$ and $C_{14}$ alcohols containing varying amounts of monoglycoside (DP1). The results can be seen from the following Table 4.

TABLE 4

| Alkyl Group | % DP1 (by weight) | Viscosity (cps) |
| --- | --- | --- |
| $C_{12}$ | 60.1 | 810 |
| $C_{12}$ | 48.1 | 157 |
| $C_{12}$ | 37.6 | 8 |
| $C_{14}$ | 48.9 | 30,750 |
| $C_{14}$ | 37.6 | 1,213 |
| $C_{14}$ | 29.8 | 9 |

It can be seen from the foregoing that low viscosities below 10 are achieved with the longer chain ($C_{14}$) alkyl polyglycoside at monoglycoside content below 35%, about 30%. With the shorter chain ($C_{12}$) alkylpolyglycoside, the low viscosity, below 10 cps. is achieved at a level below about 40%.

In order to achieve these low viscosities, the monoglycoside content should be below 40%, preferably below about 35%, the average DP should be above 1.8, and well less than about 20% of polyglycosides of DP5 and higher.

As indicated earlier, the removal of the monoglycoside from an essentially Flory distribution of monoglycoside and polyglycoside provides a polyglycoside having enhanced surfactant properties. When about half of the monoglycoside is separated from a Flory distribution reaction product, the polyglycoside having DPs of 2 and 3, originally present, are retained and accordingly present in the resulting polyglycoside product remaining. If the monoglycoside content of the initial Flory distribution is typically on the order of about 50–70% by weight as noted earlier, the remaining polyglycoside product will accordingly after removal of the monoglycoside by molecular distillation, or other method, contain about 25–35% diglycoside and the average DP of the resulting composition above about 1.8 to about 2.8. The resulting product will have an HLB in the range of about 10 to about 18, preferably about 12 to about 16, the HLB range which is most desirable for surfactant application.

In an alkylpolyglycoside product resulting from the reaction of an acid alkanol and a saccharide in the s presence of an acid catalyst, as described earlier contain various fractions of degrees of polymerization. The presence of polar glycoside fractions in the product, which may be designated as those having a DP of 5 and higher, have been found to have low laundry cleaning or surfactant activity, such fraction having HLB values of about 16 and higher. The presence of such polar fractions, however, were found not to reduce the cleaning action or surfactant activity of the DP2, DP3 and DP4 fraction present now in higher or maximized levels in the polyglycoside product remaining after removal of the monoglycoside, particularly after removal of half or more of the monoglycoside. As indicated, the level in the product of these polar fractions are preferably maintained at less than about 20%, and preferably less than about 10 or 15%. With the removal of the monoglycoside as described in the present invention, these polar fractions will also be more concentrated in the resulting polyglycoside. With a typical Flory distribution described earlier, removal of the monoglycoside to the extent of only about 10% monoglycoside is retained in the resulting polyglycoside, the polar fractions will be below the levels noted above. Small amounts of monoglycosides in the resulting polyglycoside were found not to be deleterious to the surfactant or detergent activity of the product. As the amounts of monoglycoside increase to above about 25%, the surfactant performance of the product tends to be affected due to surface properties of the monoglycoside itself and its effect on lowering the overall average DP to the lower level of about 1.8.

By use of the present invention, the isomer distribution in the alkyl polyglycoside product may be controlled or adjusted to provide improved surfactant or detergency properties to the extent that the product may function as a stand-alone surfactant, tending to match the performance of Neodol 25-7 (an ethoxylated [7EO] alcohol having mixed $C_{12}$ to $C_{15}$ alkyl groups), typically considered a standard for stand-alone properties, against which other products are compared, particularly in laundry cleaning application on dust/sebum soiled cloth using cotton and polyester/cotton (Dacron/cotton) cloth. The results of laundry cleaning action of a "peaked" product (a peak of DP2 or DP 2 plus DP 3) compared to Neodol 25-7 can be seen from the following example.

EXAMPLE 6

Pure alcohol cuts of alkyl polyglycoside surfactants were prepared (a $C_{11}$, $C_{12}$ and $C_{14}$), the peaked residues described in Example 3. The samples were then tested and evaluated for Draves Wetting Time, Ross Miles Foam Height and Laundry Detergency.

The test conditions were as follows:
Draves Wetting Time—run at room temperature (77° F.) using 0.1 wt. % surfactant solution. Wetting times were also run at varying concentrations to obtain a 20-second wetting time.

Ross Miles Foam Height-modified—run at room temperature (77° F.) using 0.1 wt. % surfactant solution.

Laundry Detergency Testing—used 1 liter of 150 ppm (Ca:Mg, 3:2) containing TEA (buffer) at a temperature of 100° F. The soil cloth was (Scientific Services) Dust Sebum Cotton and Dacron/Cotton. The total cleaning units is the reflectance of soiled cloth after washing minus reflectance of soiled cloth before washing. A difference of three cleaning units is needed to say there is a difference in cleaning action between products.

The results of the Draves Wetting Time and Ross Miles Foam Height can be seen from the following Table 5A:

TABLE 5A

| Alkylpolyglycoside Surfactant | 77° F. Draves Wetting | Foam (mm) 77° F. 0 min. | 5 min. |
|---|---|---|---|
| Regular $C_{11}$ | 260 sec | 120 | 120 |
| Peaked $C_{11}$ | 47 sec | 155 | 155 |
| Regular $C_{12}$ | 20 sec | 103 | 103 |
| Peaked $C_{12}$ | 42 sec | 156 | 156 |
| Regular $C_{14}$ | 92 sec | 40 | 40 |
| Peaked $C_{14}$ 1 | 70 sec | 98 | 98 |
| Peaked $C_{14}$ 2 | 315 sec | 80 | 80 |

1 Contains approximately 25% DP1 Glycoside
2 Contains approximately 10% DP1 Glycoside Table 5B, below, illustrates the amount of surfactant needed to get a 20-second wetting time for the $C_{11}$ and $C_{12}$ regular (R) and peaked (P) products:

TABLE 5B

| Time | % Surfactant Solution | | | |
|---|---|---|---|---|
| (Seconds) | $C_{11}$ (R) | $C_{11}$ (P) | $C_{12}$ (R) | $C_{12}$ (P) |
| 20 | 0.21 | 0.23 | 0.10 | 0.24 |

The improvement in laundry detergency of the peaked product compared to the original alkyl polyglycoside surfactant can be seen from the following Table 5C. In all cases the peaked products have more cleaning ability than the original regular product, and approach the Neodol 25-7, a linear alcohol ethoxylate, shown in the Table.

TABLE 5C

| g/l Surfactants | Cleaning Units | | | | | | |
|---|---|---|---|---|---|---|---|
| | $C_{11}$ (R) | $c_{11}$ (P) | $C_{12}$ (R) | $C_{12}$ (P) | $C_{14}$ (R) | $C_{14}$ (P) | Neodol |
| .12 | 4.6 | 8.1 | 16.4 | 21.2 | 16.6 | 20.8 | 24.2 |
| .24 | 5.3 | 20.2 | 22.3 | 24.2 | 19.9 | 22.6 | 29.8 |
| .36 | 7.7 | 24.6 | 24.3 | 25.2 | — | — | 29.6 |

As indicated earlier, an alkylpolyglycoside composition having a preselected or predetermined average alkyl chain length and surfactant properties can be prepared from the at least binary mixture alkylpolyglycoside compositions prepared commercially as described above. After selecting the predetermined average carbon chain length of the alkyl moiety, the composition having the desired detergent or surfactant properties is prepared by mixing two or more of at least binary components, each binary component having an average alkyl chain length such that, when mixed, the amounts of the binary components are effective to provide the predetermined selected average alkyl moiety and the surfactant properties. Not only are properties improved with mixtures of typical Flory distribution products, but also with mixtures of the peaked products of the present invention. The peaked products from which substantial amounts of monoglycoside have been removed, when mixed using binary components as discussed above, will provide improved foaming over mixtures of the typical Flory distribution products. Further, it was found that improvement in foam properties of an individual binary component of a peaked product may be improved by the addition of a monoglycoside having an alkyl chain different from that of the binary component of a peaked product. Thus, it has been found that the addition of the monoglycoside which was reserved from a $C_{8,10}$ Flory distribution to also provide a $C_{8,10}$ peaked product, may be added to a $C_{12,14,16}$ peaked product, and provide improved foam properties over those of (a) the peaked $C_{8,10}$ or (b) peaked $C_{12,14,16}$, (c) the mixture of peaked $C_{8,10}$ and $C_{12,14,16}$ and (d) the mixture of typical Flory distribution of $C_{8,10}$ and $C_{12,14,16}$ products.

By "at least binary component" as the term is employed herein is meant to include compositions having at least two different alkyl chain length polyglycosides, and accordingly includes ternary mixtures containing three different alkyl chain length polyglycosides. Thus, the composition may contain a mixture of $C_8$–$C_{10}$, $C_{10}$–$C_{12}$, $C_{12}$–$C_{13}$, $C_{12}$–$C_{16}$, $C_{12}$–$C_{14}$, $C_{14}$–$C_{15}$, $C_{16}$–$C_{18}$, as well as one containing $C_9$–$C_{10}$–$C_{11}$, $C_{12}$–$C_{14}$–$C_{16}$ alkylpolyglucosides, or the like.

Unexpectedly, it was found that mixing the at least binary compositions having differing alkyl moieties as described above affords an opportunity to formulate to a wide variety of desired and preselected surfactant or detergent properties and provides for improved overall properties of the mixture. Accordingly, the present invention affords a unique and surprising approach to preparing alkylpolyglycoside compositions having not only a designated average alkyl chain length, which chain length has a predominant impact on HLB and other properties, but also the higher DPs achieved by removal of monoglycoside to provide the peaked alkylpolyglycosides described earlier above. By taking any two or more binary components and mixing these to provide a designated average alkyl chain length, surprisingly and unexpectedly it was found that the composition retains the beneficial effects of each of the binary components while providing the desired HLB and surfactant properties.

As indicated earlier, the improved alkyl glycoside compositions prepared by mixing two or more of at least binary components containing alkylpolyglycosides of varying alkyl chain lengths in amounts to provide surfactant properties of a preselected average alkyl chain length. This is preferably achieved by mixing at least two binary components, one of which has an average alkyl chain length below the preselected average alkyl chain length and the other binary component has an average alkyl chain length greater than the preselected average chain length. Thus, if an alkylpolyglycoside of the preselected average alkyl chain length desired, which may be designated as $R_{sp}$ herein, has a chain length of N number of carbon atoms, one binary component will have a lower average chain length alkylpolyglycoside, in which the R group may be designated as $R_c$, will have less than N number of carbon atoms (i.e., $R_c < R_{sp}$), while the other binary component will have average higher chain length alkyl groups, which may be designated $R_{hc}$, and will have more than N number of carbon atoms (i.e., $R_{hc} > R_{sp}$).

In a preferred embodiment there is a difference of at least one carbon atom between the lower and higher average chain lengths of the binary components being mixed to attain surfactant properties of a product having the preselected chain length.

Since the resulting compositions of the mixture is reached by mixing at least two binary components having a lower average chain length, with individual glycoside chain length of about 8 to about 18, and a higher average chain length, the resulting average chain length preselected will lie in the range of about 9 to about 14, preferably about 9 to about 12. For surfactant properties, the HLB of the resulting from the mixtures composition will have a range of about 10 to about 16, and preferably about 11 to about 14. The average DP of the composition resulting from the mixture will be in the range of about 1.2 to about 3, preferably in the range of about 1.4 to about 2.5.

The following examples serve to illustrate, but not limit, the invention. The examples which follow include those of U.S. application Ser. Nos. 07/774,430 and 07/876,967, noted earlier, which deal with mixtures of binary components of alkylpolyglycosides having a typical Flory distribution as well as mixtures of binary components of alkylpolyglycosides from which monoglycosides have been removed. All parts and percentages in the examples are by weight, unless otherwise noted. In the examples to follow, commercially available alkylpolyglycosides available from Henkel Corporation which were employed, are as follows:

1. APG® Surfactant 225—an alkylpolyglycoside in which the alkyl group contains 8 and 10 carbons from a mixture of mixed $C_8$ and $C_{10}$ alkanols, in which the alkyl chain by weight % contains 45% $C_8$ and 55% $C_{10}$, and having an average DP of 1.6, an average lipophile chain (alkyl group), i.e., R equal to 9.1 and an HLB of 13.6.

2. APG® Surfactant 325—an alkylpolyglycoside in which the alkyl group are a mixture of $C_9$, $C_{10}$ and $C_{11}$ chains in a weight ratio respectively of 20:40:40, having an average DP of 1.6, an average lipophile chain of 10.2 and an HLB of 13.1.

3. APG® Surfactant 625—an alkylpolyglycoside in which the alkyl groups are a mixture of $C_{12}$, $C_{14}$ and $C_{16}$ chains in a weight ratio respectively of 68:26:6, and having an average DP of 1.6, an average lipophile chain of 12.76 and an HLB of 12.1.

4. APG® Surfactant 300—an alkylpolyglycoside substantially the same as the 325 product above but having an average DP of 1.4 and an HLB of 12.6.

5. APG® Surfactant 600—an alkylpolyglycoside substantially the same as the 625 product above but having an average DP of 1.4 and an HLB of 11.5.

In the examples in which peaked products are employed, these were obtained by molecular distillation of the APG® surfactants 225 and 625 above. The monoglycoside and polyglycoside fractions resulting are designated as follows:

(1) 201—monoglycosides from APG® 225 surfactant above, about 98% $C_8$, $C_{10}$ monoglycosides fraction, (2) 202—polyglycosides from APG® 225 surfactants, $C_8$, $C_{10}$ polyglycosides having a DP of about 2.2.

(3) 601—monoglycosides from APG® 625 surfactant above, about 98% $C_{12}$, $C_{14}$, $C_{16}$ monoglycoside fraction (4) 602—polyglycosides from APG® 625 surfactant above, $C_{12}$, $C_{14}$, $C_{16}$ polyglycosides having a DP of about 2.2.

EXAMPLE 7

In this example, a composition to be prepared from the commercially available APG® 225 and 625 surfactants above, was selected to substantially equal the alkyl average chain length of 10.2 of the 325 product produced from an oxo alcohol mixture containing alkyl groups containing both an even and an odd number of carbon atoms but employing alkylpolyglycosides from natural alkanols containing even number of carbon atom chains. The APG® 225 product containing a mixture of short chain $C_8$ and $C_{10}$ chain lengths was mixed with APG® 625 containing a mixture of long chain $C_{12}$, $C_{14}$ and $C_{16}$ chain lengths in a 2:1 ratio by weight to provide a resulting product having an average carbon chain length of 10.3, a calculated HLB of 13.1.

The product was evaluated by the following tests:

1. Ross Miles Foam—ASTM No. D1173-53. Foaming characteristics are measured of 0.1% active solutions made with deionized (DI) water in an apparatus that drops a 200 ml sample into 50 ml of the same solution. The test solutions are evaluated at 25° and 49° C. and the foam generated is measured in millimeters (mm) at 1 minute and again after an additional 5 minutes.
2. Blender Foam—measures the foaming properties with high agitation.
   a. Foam height is determined by measuring (in mm) the quantity of foam generated by 100 ml. of 0.9% active solutions mixed at high speed in a blender for 1 min. The test is run at 25° C. and uses water containing 150 ppm water electrolytes.
   b. Foam separation measures how quickly (in sec) 50% of the liquid phase (the 100 ml. test sample described above) is recovered from the foam phase.
   c. Foam flow measures the body of the foam by using 200 ml. of the same solution (0.9% actives) that is mixed in a blender for 1 min. The blender is opened and held inverted for 15 seconds over a funnel which is resting on a 20-mesh sieve. The funnel is modified with a wire across the diameter, 8 cm from the bottom. The time is recorded (in sec) from when the blender is inverted until the wire in the funnel becomes visible as the lather drains out.
3. Draves Wetting—ASTM No. D2281-68. The wetting ability of the surfactants is measured by the time it takes for a 0.1% active solution in DI water at pH 7 to completely saturate a cotton skein allowing it to sink in a 500 ml graduated cylinder.
4. CMC—The critical micelle concentration (CMC) was determined by the Wilhemy Plate Method using a Cahn Balance.
5. IFT—Interfacial tensions were measured using the spinning drop technique with mineral oil. A Spinning Drop Interfacial Tensiometer, Model 500 from the University of Texas, measures the interfacial tensions of 0.1% active solutions in DI water as dynes/cm.
6. HLB—The Hydrophilic-Lipophilic Balance was calculated for each blend using the procedure of dividing the weight percent of the hydrophile by 5.

The following Table 6 is a summary of the results comparing the blends of the 225 and 625 mixtures with that of the 325 product and of the individual 225 and 625 products.

TABLE 6

| Ratio<br>APG ® Surfactant | 325 | 225 | 2:1<br>(225:625) | 625 |
|---|---|---|---|---|
| Average Carbon Chain | 10.2 | 9.1 | 10.3 | 12.8 |
| ROSS MILES Initial | 140 | 140 | 140 | 110 |
| (25° C., mm) 5 min | 140 | 135 | 135 | 110 |
| ROSS MILES Initial | 190 | 160 | 190 | 175 |
| (49° C., mm) 5 min | 190 | 160 | 190 | 175 |
| Draves Wetting (sec) | 15 | 240 | 35 | 28 |
| HLB (calc) | 13.1 | 13.6 | 13.1 | 12.1 |
| CMC (weight %) | 0.0178 | 0.0285 | 0.00521 | 0.00346 |
| IFT, 0.1% (dyn/cm) | 1.6 | 2.9 | 1.0 | 1.1 |
| Blender Foam, Initial | 95 | 100 | 95 | 35 |
| (25° C., mm) 5 min | 80 | 90 | 80 | 25 |
| Foam Separation (min) | 2:20 | 3:00 | 2:20 | 1:45 |
| Foam Flow (sec) | 3 | 19 | 4 | 0 |

The foregoing shows that the 2:1 mixture of the 225 and 625 products is superior in foam properties to either of the 225 or 625 product alone while matching the characteristics of the 325 product. The CMC and IFT are significantly lower than the values for the 225 product and lower than the 325 product and about the same level of the 625 product. Thus, the 2:1 mixture product of the present invention, provides superior surfactant surface properties with low CMC and IFT.

EXAMPLE 8

In the same manner as Example 7, blends of the 225 and 625 products were made at other ratios up to 9:1 and evaluated. Table 7 below is a summary of the test results in which the 2:1 test data of Example 1 is also included along with the other ratios of 225:625 as shown.

TABLE 7

| APG ®<br>Surfactant | | | 225:625 | | | | | |
|---|---|---|---|---|---|---|---|---|
| Ratios | 325 | 225 | 9:1 | 4:1 | 3:1 | 2:1 | 1:1 | 625 |
| Average Carbon Chain | 10.2 | 9.1 | 9.5 | 9.8 | 10.0 | 10.3 | 11.0 | 12.8 |
| ROSS MILES Initial | 140 | 140 | 135 | 135 | 140 | 140 | 140 | 110 |
| (25° C., mm) 5 min | 140 | 135 | 130 | 130 | 135 | 135 | 140 | 110 |
| ROSS MILES Initial | 190 | 160 | 200 | 200 | 195 | 190 | 195 | 175 |
| (49° C., mm) 5 min | 190 | 160 | 190 | 195 | 190 | 190 | 190 | 175 |
| Draves Wetting (sec) | 15 | 240 | 75 | 38 | 36 | 35 | 32 | 28 |
| HLB (calc) | 13.1 | 13.6 | 13.4 | 13.3 | 13.2 | 13.1 | 12.8 | 12.1 |
| CMC (weight %) | 0.0178 | 0.0285 | — | — | — | 0.00521 | — | 0.00346 |
| IFT, 0.1% (dyn/cm) | 1.6 | 2.9 | — | — | — | 1.0 | — | 1.07 |
| Blender Foam, Initial | 95 | 100 | 105 | 105 | 100 | 95 | 85 | 35 |

TABLE 7-continued

| APG ® Surfactant | | | 225:625 | | | | | |
|---|---|---|---|---|---|---|---|---|
| Ratios | 325 | 225 | 9:1 | 4:1 | 3:1 | 2:1 | 1:1 | 625 |
| (25° C., mm) 5 min | 80 | 90 | 90 | 90 | 90 | 80 | 80 | 25 |
| Foam Separation (min) | 2:20 | 3:00 | 2:50 | 2:35 | 2:35 | 2:20 | 2:00 | 1:45 |
| Foam Flow (sec) | 3 | 19 | 11 | 7 | 4 | 4 | 3 | 0 |

EXAMPLE 9

In this example the 2:1 mixture of the 225 and 625 products were evaluated for caustic solubility at 25° C. The results are shown in Table 8, in which data for the 225, 325 and 625 products individually are also shown. The percentage of each alkylglycoside that is soluble in the various levels of caustic (NaOH) is shown. Solubility is qualified as the level of glycoside which results in a clear, homogenous solution.

TABLE 8

| | % APG in | | | | |
|---|---|---|---|---|---|
| APG ® | 0% NaOH | 10% NaOH | 20% NaOH | 30% NaOH | 40% NaOH |
| APG ® 225 | 73 | 60 | 45 | 35 | 28 |
| APG ® 325 | 56.5 | 41.5 | 24.5 | 14 | 5.5 |
| 225/625 (2:1) | 64.5 | 53 | 43 | 34 | 26 |
| APG ® 625 | 33 | 25 | 11 | 2 | 0 |

The foregoing illustrates the superior solubility of the mixture of at least two lower short chain with at least two higher or longer chain glycosides which provides a broader base of fatty chains from $C_8$ to $C_{16}$ in the product in contrast to the individual narrower base of the individual 225, 325 or 625 polyglycoside products. This advantage in solubility indicates the suitability of the 225:625 mixture in the 2:1 ratio by weight in hard surface cleaning formulations which employ NaOH.

In the cleaning formulations, the alkylpolyglycoside of the present invention is employed with adjuvants commonly or usually associated with cleaner applications. The alkylpolyglycoside is employed alone, or preferably, with other co-surfactants, particularly anionic surfactants, such as ethoxylated, or unethoxylated, long chain (8 to 22 carbon) alcohol sulfates or sulfonates.

EXAMPLE 10

A Gardner cleaning evaluation ASTM No. D4488-85 was conducted for 3:1, 2:1 and 1:1 blends of the 225 and 625 product, in which mechanical soil removal tests were performed to measure the relative ability of the surfactants to remove a standard soil (A3) from white vinyl tiles using a Gardner Straight Line Washability Machine. The procedure utilizes a Labscan Reflectometer to measure the initial reflectance of clean white vinyl tiles prior to soiling and then after washing with a sponge for 20 cycles in test solutions of 0.6% active surfactant in DI water at 25° C.

The calculation is typical for this type of cleaning test where the cleaning ability of water alone is used as the baseline:

$$\% \text{ SOIL REMOVED} = \frac{RF - RH_2O}{RI - RH_2O} \times 100$$

The results of the test showed the blends to be slightly less effective than the 325 alone, but the 3:1 and 2:1 blends are within the 3% of soil removal requirement.

The foregoing examples illustrate the method of preparing compositions of the present invention. Specifically, a selection of a predetermined average alkyl chain length of about 10.2 (above about 9 and below about 12) was made for the alkyl moiety to provide a surfactant composition having an HLB of about 13 and a DP of about 1.6. The predetermined or selected composition was then prepared by mixing or blending a mixture of a $C_8$ and $C_{10}$ alkylpolyglycoside (alkyl group lower in chain length than the selected average chain length of 10.2) with a mixture of a $C_{12}$, $C_{14}$ and $C_{16}$ alkylpolyglycoside (alkyl group higher in chain length than the selected chain length of 10.2). The resulting products in ratios of up to 9:1 of the lower and higher chain length provided a surfactant composition having an HLB of about 13 and exhibiting foam properties superior to the individual mixtures of $C_8$ and $C_{10}$ alone or the $C_{12}$, $C_{14}$ and $C_{16}$ alone, with low CMC and IFT properties. The products have superior solubility in caustic thus providing compositions which can be formulated into hard surface cleaner compositions. The products can also be formulated for soil removal or laundry detergent compositions. The compositions also find utility in widely diverse applications such as coal dust suppressant compositions, flotation of ores, particularly non-sulfidic ores such as cassiterite, corrosion inhibitor compositions and contact lens cleaning compositions.

The compositions also have surfactant properties particularly suitable for use in the cosmetic industry for formulation into personal care products, including mild shampoos and mild children's liquid soaps, as well as lotions and creams. The compositions are particularly useful in toothpastes and mouthwash formulations as well as antiperspirant applications.

EXAMPLE 11

In this example, blends of two binary fractions were evaluated to provide an alkylpolyglycoside composition having surfactant properties suitable for cosmetic industry application. The test method employed in the evaluation was a foam method acceptable to the cosmetic industry, which is carried out with, and without the use of a synthetic sebum composition. The foam test methodology is as follows:

Prepare a 10% aqueous solution of product being evaluated. Add four (4) grams of this solution to 146 grams of water (hardness 50 ppm) heated to 29° C. ±1° C. Agitate for five (5) seconds in a Sears electronic blender with microprocessor control, medium/No. 5 speed agitation. Transfer the foam into a 500 ml graduated cylinder. Measure the initial foam volume to the nearest 5 ml and then record the position of the foam/water interface after 3.5 minutes. This later reading represents the foam drainage.

When testing with synthetic sebum, 0.5 grams synthetic sebum is added to product prior to preparing the 10% aqueous solution, after which the test is run as described above. The synthetic sebum employed has the following composition.

| Ingredient | % by Weight |
|---|---|
| Palmitic Acid | 10.00 |
| Stearic Acid | 5.00 |
| Coconut Oil | 15.00 |
| Paraffin | 10.00 |
| Spermaceti | 15.00 |
| Olive Oil | 20.00 |
| Squalene | 5.00 |
| Cholesterol | 5.00 |
| Oleic Acid | 10.00 |
| Linoleic Acid | 5.00 |
| | 100.00 |

In testing for foam the foam tests were repeated five times and an average taken. In the data in Table 9 below, the first figure reported is the foam height and the second reading is taken 3.5 minutes later and represents foam drainage.

TABLE 9

| Sample | | Foam Results | |
|---|---|---|---|
| Weight Ratio | Alkylpolyglycoside | With Sebum | Without Sebum |
| 4:1 | APG 225/625 | 250/140 | 255/140 |
| 3:1 | " | 265/135 | 260/145 |
| 2.5:1 | " | 265/135 | 265/145 |
| 2:1 | " | 267/135 | 275/135 |
| 1.5:1 | " | 270/135 | 275/145 |
| — | APG 225 | 190/142 | 200/140 |
| — | APG 300 | 280/135 | 290/137 |
| — | APG 325 | 260/135 | 275/135 |
| — | APG 625 | 240/145 | 260/145 |
| — | APG 600 | 250/145 | 255/140 |
| 4:1 | APG 225/APG 600 | 265/135 | 270/135 |
| 3:1 | " | 275/135 | 270/135 |
| 2.5:1 | " | 277/135 | 285/135 |
| 2:1 | " | 280/135 | 290/137 |
| 1.5:1 | " | 280/135 | 290/135 |

From the foregoing, it can be seen that employing weight ratios of 2:1 or 1.5:1 of the 225 binary fraction with the APG® 600 or 625 ternary fractions a composition results which meets the foaming properties of the APG® 300 or 325 products which find utility in the cosmetic industry. The data also indicates a degree of synergism in weight ratios up to about 4:1, providing a means for formulating compositions using commercial products comprised of at least binary mixture or fractions, to designated desired average carbon chain lengths and desired HLB values. With the range of about 1.5:1 to about 4:1 of the APG® 225 (which contains 45% $C_8$ and 55% $C_{10}$) to the APG® 625 (which contains 68% $C_{12}$, 26% $C_{14}$ and 6% $C_{16}$), the $C_{10}$ species will predominate in the mixture, which species will predominate in any mixture of APG® 225 and APG® 625, in which the weight ratio in the mixture of APGO 225 to APG® 625 is above about 1.25:1.

EXAMPLE 12

In this example, a mixture of binary components of peaked products (202 and 602) were evaluated for foam (Ross Miles) and compared to individual commercially available binary components (APG® surfactant 225 and APG® surfactant 625) as well as a mixture thereof of both the 225 and 625 components.

The results in Ross Mile foam can be seen from the following Table 10, in which the data from Table 7 is included for the individual 225 and 625 products and mixture thereof in ratio of 1:1, 2:1 and 4:1 of 225:625.

TABLE 10

| Alkylpolyglycoside | Ross Miles Foam (min. at 25° C.) | Ross Miles Foam (min. at 49° C.) |
|---|---|---|
| 225 | 135–140 | 160 |
| 625 | 110 | 175 |
| 225:625 | | |
| 4:1 | 130–135 | 195–200 |
| 2:1 | 135–140 | 190 |
| 1:1 | 140 | 190–195 |
| 202:602 | | |
| 4:1 | 165 | 170 |
| 2:1 | 170 | 185 |
| 1:1 | 160 | 170 |

As can be seen from the foregoing, the mixture of two peaked binary components provided significantly higher foam at 25° C. than the individual binary components (225 and 625) or the mixture thereof (225:625).

EXAMPLE 13

In this example, is illustrated the results of the Draves Wetting and CMC evaluation. Again, the data from Table 7 for the 225 and 625 products and mixtures thereof are included in the following Table 11.

TABLE 11

| Alkylpolyglycoside | Draves Wetting (sec.) | CMC (weight %) |
|---|---|---|
| 225 | 240 | 0.0285 |
| 625 | 28 | 0.00346 |
| 225:625 | | |
| 4:1 | 38 | |
| 2:1 | 35 | .00521 |
| 1:1 | 32 | |
| 202:602 | | |
| 4:1 | 60 | 0.0108 |
| 2:1 | 65 | 0.0040 |
| 1:1 | 90 | 0.0036 |

As can be seen from the foregoing, while the Draves Wetting results of the mixture of peaked binary components (202:602) is somewhat higher than those of the mixture of binary components with typical Flory distribution (225:625) the CMC is lower, on the order of magnitude of the 625 product.

EXAMPLE 14

In addition to the Ross Foam, Draves Wetting and CMC results in Examples 12 and 13 above in relation to the individual 225 and 625 binary components, mixtures thereof and mixtures of the molecularly distilled 225 and 625 components to provide the 202 and 602 peaked fraction alkylpolyglycosides, Ross Foam, Draves Wetting and CMC results were investigated on the monoglycoside fraction 201 and 601 individually, and a mixture thereof, and mixtures of the monoglycosides fraction 201 with the peaked alkylpolyglycoside 602 and the monoglycoside fraction 601 with the peaked alkylpolyglycoside 202. The results can be seen from the following Table 12.

TABLE 12

|  | ROSS MILES FOAM @ 25° C. (mm) | ROSS MILES FOAM @ 49° C. (mm) | DRAVES WETTING (sec) | CMC (wt %) |
|---|---|---|---|---|
| 201 | 165 | 180 | 15 | 0.0456 |
| 202 | 140 | 155 | 240 | 0.0335 |
| 601 | 50 | 55 | 42 | 0.0013 |
| 602 | 155 | 160 | 48 | 0.0021 |
| 4:1 201:601 | 155 | 170 | 21 | 0.0036 |
| 2:1 201:601 | 140 | 165 | 26 | 0.0034 |
| 1:1 201:601 | 85 | 155 | 36 | 0.0033 |
| 4:1 201:602 | 180 | 190 | 21 | 0.0038 |
| 2:1 201:602 | 175 | 185 | 27 | 0.0039 |
| 1:1 201:602 | 170 | 175 | 36 | 0.0038 |
| 4:1 202:601 | 140 | 160 | 47 | 0.0039 |
| 2:1 202:601 | 120 | 150 | 43 | 0.0039 |
| 1:1 202:601 | 100 | 130 | 43 | 0.0039 |
| 4:1 202:602 | 165 | 170 | 60 | 0.0108 |
| 2:1 202:602 | 170 | 185 | 65 | 0.0040 |
| 1:1 202:602 | 160 | 170 | 90 | 0.0036 |

An unexpected, interesting result is seen particularly in the mixtures of the monoglycoside $C_8$, $C_{10}$ fraction (201) with the peaked polyglycoside $C_{12}$, $C_{14}$, $C_{16}$ fraction (602). Viewing the foam results it can be seen that the foam results of this mixture are higher than the individual fraction and the mixtures of the peaked $C_8$, $C_{10}$ and $C_{12}$, $C_{14}$, $C_{16}$ (the 202 and 602) and by reference to Table 10, higher than the APG® 225 and the APG® 625 binary components individually, or the mixture thereof. The Draves Wetting values of the 201 and 602 mixture are comparable to the mixture of the 225 and 625 binary components shown in Table 10 and the CMC values correspond substantially to the value of the 202 and 602 binary component mixture. Accordingly, the results indicate that the properties of a peaked alkylpolyglycoside may be modified by the addition of some alkylmonoglycoside of a different alkyl chain length from that of the peaked alkylpolyglycoside, particularly when the alkylmonoglycoside has a shorter average alkyl chain length in relation to the peaked (high DP) longer chain length alkylpolyglycoside. As indicated in the discussion following Example 3 and Table 2, the purified monoglycoside stream of the present invention will find utility in applications where monoglycosides find utility or for conversion to their derivatives. The foregoing data in Table 12 illustrates still another utility for such a purified alkylmonoglycoside, namely the addition to a peaked alkylpolyglycoside in which the alkyl chain length differs from that of the alkyl chain of the monoglycoside composition to modify the properties.

In view of the foregoing examples, the present invention accordingly encompasses the preparation of an alkylpolyglycoside composition in which the alkyl moiety contains from about 6 to about 18 carbon atoms and in which the average carbon chain length of the composition is from about 9 to about 14 comprising a mixture of two or more of at least binary components of alkylglycosides in which one of the binary components has a lower average chain length than the other binary components, and wherein the binary component having the lower average chain length and each other binary component is present in the mixture in relation to its average carbon chain length to provide the surfactant composition with the average carbon chain length of about 9 to about 14 and an HLB in the range of about 10 to about 16, and wherein at least one or all of the binary components comprise a non-Flory distribution of glycosides comprised of a mixture of an alkyl monoglycoside and a mixture of alkylpolyglycosides having varying degrees of polymerization of 2 and higher in progressively decreasing amounts, in which the amount by weight of polyglycoside having a degree of polymerization of 2, or mixture thereof with the polyglycoside having a degree of polymerization of 3, predominate in relation to the amount of monoglycoside, said non-Flory distribution binary component having an average degree of polymerization of about 1.8 to about 3.

The examples above illustrate that significant results are achieved by the alkylpolyglycosides mixtures of the present invention of either Flory or non-Flory distribution binary components, even in the absence of any co-surfactants. While the mixtures may be employed without added surfactants, their use in formulations for is various end-use applications, provides for significant, advantageous properties in such formulations employing other co-surfactants. For example, anionic surfactants are generally highly irritative to the skin. However, when the alkylpolyglycoside mixtures of the present invention are employed in formulations employing anionic surfactants, it was found that the formulated composition was no longer highly irritative to the skin and, accordingly, the alkylpolyglycoside mixture finds special utility in cosmetic, particularly personal care, products and applications, where mild or non-irritative properties are particularly desirable, such as shampoos, foam baths, hand soaps, hair conditioners, and facial cleansers. Thus the alkylpolyglycoside surfactant compositions of the present invention offer formulation ease with good foaming and cleaning power of an anionic surfactant and further offering mildness to skin and eyes. While noting their use with anionic surfactants, the alkylpolyglycoside surfactants of the present invention may stand alone as the primary surfactant or are also compatible with other surfactant types (including nonionic, cationic and amphoteric), providing improved performance of the formulations therewith.

In end-use formulations, the alkyl polyglycosides resulting from the present invention will typically be present in amount from ½ to about 80% and more typically about 30, 50 or 70% in an aqueous solution form. A granule form of the alkyl polyglycoside may be prepared by spray drying an aqueous solution of the polyglycoside and adjuvants to provide a substantially dry, non-sticky granule. In such a product, the alkylpolyglycoside may comprise up to about 98–99% of the granule with very little water or other solvent, along with any optional adjuvants. The composition will utilize other compatible ingredients, which will vary dependent on the specific end-use application desired, the various end-use application having been discussed earlier referring to many patents. Thus, the compositions may contain other surfactants, detergency builders, soil-suspending agents, brightening agents, abrasives, dyes, fabric-conditioning agents, hair conditioning agents, hydrotropes, solvents, fillers, etc. Such materials assist the alkyl polyglycoside in its end-use application, and are, accordingly, auxiliary, optimal, reagents referred to herein as "adjuvants." Formulations for various end-use applications, accordingly, may generally comprise:

(a) Alkyl polyglycoside surfactant of the present invention in an amount of about 0.5 to 99% by weight, (b) Solvent (water or other non-aqueous liquid or mixtures thereof), in an amount of about 0.5 to about 99.5% by weight and (c) Adjuvant (optional ingredient based on particular end-use application) in an amount up to about 99.5% by weight.

The anionic surfactants include any of the surfactants commonly classified as anionic surfactants. These surfactants include the alkali metal, ammonium and magnesium salts of the alpha olefin sulfonates, alkyl sulfonates, alkyl aryl sulfonates, alkyl aryl ether sulfates, alkyl ether sulfates, sulfated alcohol ethoxylates, taurates, petroleum sulfonates, alkyl naphthalene sulfonates, alkyl sarcosinates and the alkyl sulfosuccinates in which the alkyl group is preferably a long chain 8 to 22 carbon atom group and the aryl group is preferably phenyl or naphthyl. Typical surfactants which fall within the above description include sodium lauryl sulfonate, ammonium lauryl sulfonate, ammonium lauryl sulfate, dodecyl benzene sulfonate, sodium lauryl sulfate, sodium lauryl ether sulfate, sodium lauryl myristyl sulfate, diethanolamine lauryl sulfate, ammonium salts of sulfated alcohol ethoxylates, sodium cocoyl isethionate, sodium N-methyl-N-oleoyl taurate, sodium N-methyl-N-cocoyl taurate, triethanolamine lauryl sulfate, disodium monooleamide PEG-2 sulfosuccinate, petroleum sulfonates sodium salt, alkyl naphthalene sodium sulfonates, sodium lauroyl sarcosinate, and sodium alkyl sulfosuccinate.

The amphoteric surfactants include the betaines, the sultaines, the imidazoline derivatives and the like. Typical amphoteric surfactants include ricinoleamidopropyl betaine, cocamidopropyl betaine, oleyl betaine, stearyl betaine, stearyl amphocarboxy glycinate, sodium lauraminopropionate, cocoamidopropyl hydroxy sultaine, disodium lauryliminodipropionate, tallowiminodipropionate, cocoampho- carboxy glycinate, cocoimidazoline carboxylate, lauric imidazoline monocarboxylate, lauric imidazoline dicarboxylate, lauric myristic betaine, cocoamidosulfobetaine, alkylamidophospho betaine and the like.

The nonionic surfactants preferably are the ethoxylated alcohols, including ethoxylated phenols. The preferred ethoxylated alcohols may be generally defined by the formula $R(OC_2H_4)OH$ where R is an alkyl chain of about 10 to about 18 carbon atoms and n is an average of from about 2 to about 9. Preferred alcohols are coconut alcohol, tallow alcohol and alcohols containing 12–16 carbon atoms, ethoxylated with about 6 to about 9 moles of ethylene oxide. Preferred phenols ethoxylated are the alkyl phenols containing about 6 to about 12 carbon atoms, preferably 8 to about 12 carbon atoms ethoxylated with about 5 to about 25 moles of ethylene oxide per mole of phenol, preferably about 9 to about 15 moles of ethylene oxide per mole of phenol.

The cationic surfactants which may be employed are quaternary ammonium types having at least one, and preferably two, long chain groups of about 8 to about 22 carbon atoms, preferably about 16 to 18 carbon atoms. The remaining groups are either hydrogen or preferably short chain alkyl or hydroxyalkyl groups in which the alkyl groups contain from about 1 to about 4 carbon atoms. Preferred cationic surfactants include ditallowdimethyl ammonium chloride or methyl sulfate, and dicocodimethylammonium chloride.

Typical illustrative formulations for various end-use applications are as follows:

| Ingredient | Wt % |
|---|---|
| 1. HEAVY DUTY - ALL PURPOSE HARD SURFACE CLEANER | |
| Water | 80 |
| Tetrapotassium pyrophosphate | 5 |
| Sodium metasilicate pentahydrate | 3 |
| Sodium hydroxide (50%) | 2 |
| Sodium xylene sulfonate (40%) | 5 |
| Alkyl polyglycoside (50%) | 5 |
| 2. ALUMINUM CLEANER - ALKALI | |
| Water | 58 |
| Sodium EDTA | 2 |
| Sodium gluconate | 2 |
| Sodium silicate ($SiO_2/Na_2O$ = 2.5) | 20 |
| Potassium hydroxide (45%) | 15 |
| Alkyl polyglycoside (50%) | 3 |
| 3. LAUNDRY DETERGENT | |
| (a) | |
| Alkyl polyglycoside (50%) | 30 |
| Water | 30 |
| Sodium lauryl sulfate (28%) | 35 |
| Sodium citrate | 5 |
| Optional - brighteners, color, fragrance | QS* |
| (b) | |
| Alkyl polyglycoside (50%) | 32 |
| Water | 50 |
| Sodium laureth sulfate (25%) | 8 |
| Ethoxylated fatty alcohol | 10 |
| Optional - brighteners, color, | QS* |
| 4. LIQUID HAND SOAP | |
| Alkyl polyglycoside (50%) | 16.0 |
| Water | 62.5 |
| Sodium laureth sulfate (25%) | 16.0 |
| Alkanolamide | 4.0 |
| Lanolin | .5 |
| Etylene glycol mono-stearate | 1.0 |
| Color, fragrance, preservative | QS* |
| 5. HAIR SHAMPOO | |
| Alkyl polyglycoside (50%) | 6 |
| Water | 61 |
| Sodium laureth sulfate (25%) | 30 |
| NaCl | 3 |
| Color, fragrance, preservative | QS* |

The following illustrates a typical liquid dish detergent employing an alkyl monoglycoside component (minimum of 90% monos) employed in combination with a non-glycoside surfactant.

| Ingredient | Wt % |
|---|---|
| 6. LIQUID DISH DETERGENT | |
| Alkyl monoglycoside (50%) | 18 |
| Water | 59 |
| Sodium dodecylbenzene sulfonate (60%) | 20 |
| Alkanolamide | 3 |
| Color, fragrance, preservative | QS* |

*Quantity sufficient

In the examples to follow, to illustrate formulations employing a mixture of binary components, the alkylpolyglycoside surfactant composition was a mixture of:

(a) 55.8 weight % of APG® Surfactant 200—an alkylpolyglycoside substantially the same as APG® 225 noted above in which the alkyl chain by weight contains 45% $C_8$ and 55% $C_{10}$ but having an average DP of 1.4; and (b) APG® Surfactant 600 earlier described, and containing 11.2% water. The mixture of the APG® 200 and APG® 600 alkylpolyglycosides (a weight ratio of the 200 to 600 alkylpolyglycoside of about 1.7) results in a mixture in which the $C_{10}$ species predominates. The product will be referred to in the subsequent examples as "Polyglycoside" employed as a 50% active solution in water. This surfactant composition is a mixture of binary components each having a typical Flory distribution of glycosides. However, as is clear from the earlier examples of compositions of mixtures of binary components having a peaked or non-Flory distribution, that such non-Flory distribution polyglycosides in which the average DP is from about 1.8 to about 3, and preferably within the trapezoidal area of ABCDE of FIG. 4, may be employed.

In the conventional eye irritation test, the "Polyglycoside" employed in the following examples when tested at 12% active solution, at pH 7.0, the 24-hour score is 8.0 on a scale of 0–110. Typically used anionic surfactants exhibit scores of about 30–35 in this test. In the conventional skin irritation test, at 12% active, pH of 7, the primary skin irritation index is 1.1 on a scale of 0–8. Typical anionic surfactants exhibit scores of about 4–6. Oral toxicity at 50% active, pH of 7, had 0% mortality at 5 grams per kilogram body weight, which is the cut-off point in the test.

EXAMPLE 15

This example illustrates a high-quality, high-performance shampoo that combines very low irritation with excellent foam characteristics, while leaving the hair in a very manageable condition. The ingredients and preparation are as follows:

TABLE 13

| Ingredients | % wt/wt |
| --- | --- |
| Polyglycoside | 15.0 |
| Ammonium Laureth Sulfate (Standapol ® EA-2)* | 15.0 |
| Cocamidopropyl Betaine (Velvetex ® BK-35)* | 12.5 |
| Hydrolyzed Collagen (Nutrilan ™ I)* | 1.5 |
| Citric Acid | to pH 6.0–6.5 |
| Fragrance | q.s.** |
| Water, preservative | Balance |

*available from Henkel Corporation
**quantity sufficient

The shampoo was prepared by charging the kettle with the water and adding the ingredients in the order listed while stirring. If necessary, the viscosity may be adjusted to the desired level by addition of sodium chloride. Gel-like viscosities can be obtained by adding a thickener, such as PEG-150 distearate.

EXAMPLE 16

This example illustrates a foam bath formulation which is combined with an ether sulfate to provide a foam bath with low irritation. The ingredients and preparation can be seen below:

TABLE 14

| Ingredients | % wt/wt |
| --- | --- |
| Sodium Laureth Sulfate (Standapol ® ES-3)* | 21.00 |
| Polyglycoside | 12.00 |
| Cocamidopropyl Betaine (Velvetex ® BA-35)* | 12.00 |
| Cocamide DEA | 4.00 |

TABLE 14-continued

| Ingredients | % wt/wt |
| --- | --- |
| (Standamid ® KD)* | |
| Glycol Stearate (Emerest ® 2350)* | 2.00 |
| PEG-7 Glyceryl Cocoate (Cetiol ® HE)* | 1.00 |
| Cocoyl Sarcosine (Hamposyl C)** | 1.00 |
| Kathon CG*** | 0.05 |
| Fragrance & Dyes | q.s. |
| Water | Balance |

*available from Henkel Corporation
**available from Grace Co.
***preservative available from Rohm & Haas The foam bath was prepared by charging the kettle with the water and heating the water to 60–65° C. While maintaining the temperature, the remaining ingredients are added one at a time with agitation. The pH is adjusted to 6.0–6.5, heating discontinued and the product permitted to cool to ambient temperature with continued stirring.

EXAMPLE 17

This example illustrates a mild facial cleanser combining a sulfosuccinate surfactant with the Polyglycoside. The oleyl betaine in the product functions as a skin conditioner. The ingredients and preparation can be seen from the following:

TABLE 15

| Ingredients | % wt/wt |
| --- | --- |
| Disodium Laureth Sulfosuccinate (Standapol ® SH-124-3)* | 30.0 |
| Polyglycoside | 18.00 |
| Oleyl Betaine (Velvetex ® OLB-50)* | 3.00 |
| PEG-120 Methyl Glucose Dioleate (Glucamate DOE-120)** | 2.25 |
| PEG-7 Glyceryl Cocoate (Cetiol ® HE)* | 1.50 |
| Kathon CG*** | 0.05 |
| Fragrance & Dyes | q.s. |
| Water | Balance |

*available from Henkel Corporation
**available from Americhol
***preservative available from Rohm & Haas The facial cleanser was prepared by charging the kettle with water, heating the water to 40° C. and maintaining this temperature while adding the remaining ingredients one at a time with agitation. Heating is discontinued and stirring continued until the product reaches ambient temperature, after which the pH is adjusted to 6.0–6.5.

EXAMPLE 18

This example illustrates a liquid soap for application to human skin having high foaming and yet is mild to the skin. Two skin conditioners are included. The ingredients and preparation can be seen from the following:

TABLE 16

| Ingredients | % wt/wt |
| --- | --- |
| Sodium Lauryl Sulfate (Standapol ® WAQ Special)* | 16.00 |
| Polyglycoside | 10.00 |
| Cocamidopropyl Betaine (Velvetex ® BK-35)* | 3.50 |
| PEG-150 Distearate | 2.00 |
| PPG-12-PEG-65 Lanolin Oil (Lantrol ® AWS 1692)* | 0.30 |
| Glycol Distearate (Emerest ® 2355)* | 1.00 |
| Polyacrylamidomethylpropane Sulfonic Acid (Cosmedia ® Polymer HSP-1180)* | 1.00 |
| Kathon CG** | 0.05 |
| Fragrance & Dyes | q.s. |
| Water | Balance |

*available from Henkel Corporation
**preservative available from Rohm & Haas

The liquid soap was prepared by charging the kettle with water, heating to 60–65° C. and maintaining the temperature constant while adding the ingredients one at a time under agitation. Once uniform the heating is discontinued and stirring continued until the product reaches ambient temperature, after which the pH is adjusted to 6.0–6.5 with citric acid.

In this formulation, the Lantrol® AWS 1692 and the Cosmedia® Polymer HSP-1180 functions as skin conditioners.

In personal care products for application to human skin, such as a liquid soap above, it has recently become important to include in such soaps materials generally referred to as antimicrobial agents. The term "antimicrobial" as used herein is intended to encompass generally antibacterial, antiviral, antigermicidal agents and the like. It is important that such materials when employed in personal care products for use by humans be approved by the FDA (Food and Drug Administration). A commercially available antimicrobial agent is 5-chloro-2-(2,4-dichlorophenoxy) phenol, "Triclosan", manufactured by Ciba Geigy. Such antimicrobial agents when employed are added to the liquid soap in an amount of from about 0.25 to about 1% by weight, more desirably about 0.3 to about 0.5%. A wide variety of antimicrobial agents have been described and are available for various end-use applications. "Cation DDC", a recent antibacterial agent very effective against bacteria with high resistance, finds use in disinfection in restaurants and food processing centers. "Lebon 15" is a high molecular weight amphoteric surfactant that exhibits germicidal properties. Statutory Invention Registration H269 describes germicidal quaternary ammonium halides useful in disinfectant or sanitizing cleaner compositions. German published Application DE 3,316,250 A describes N-alkylated 1-amino-1-desoxy-D-fructo-pyranose antimicrobial agents effective against fungi and bacteria. U.S. Pat. No. 4,900,721 describes disinfectants for skin and mucous membranes, which may contain one or more antimicrobial agents, such as quaternary ammonium compounds, phenols, biguanides and various others. U.S. Pat. No. 3,886,277 describes the use of 5,7-dichloro-8-hydroxy quinolines for controlling dandruff and in the background discussion describes a wide variety of substances exhibiting bacteriostatic and fungistatic properties including phenols, hexachlorophene, quaternary ammonium halides, and various sulfur-containing compounds (thio-bis compounds).

EXAMPLE 19

This example illustrates a low irritation conditioning shampoo in which the polyglycoside enhances a cationic polymer deposition, providing a two-in-one conditioning shampoo. The ingredients and preparation can be seen from the following:

TABLE 17

| Ingredients | % wt/wt |
| --- | --- |
| Polyglycoside | 12.0 |
| Sodium Laureth Sulfate (Standapol ® ES-2)* | 24.0 |
| Cocamide DEA (Standamid ® KD)* | 3.0 |
| PEG-7 Glyceryl Cocoate (Cetiol ® HE)* | 1.5 |
| Guar Hydroxypropyltrimonium Chloride (Cosmedia ® Guar C-261)* | 0.75 |
| Glycol Distearate in a surfactant base (Euperlan ® PK-810)* | 4.0 |
| Citric Acid | to pH 6.5 |
| Fragrance | q.s. |
| Water, preservative | Balance |

*available from Henkel corporation

The conditioning shampoo was prepared by charging a kettle with the water and while stirring, adding the first three ingredients in the order listed. The next two ingredients are pre-slurried and then added to the kettle after which the Euperlan® ingredient is added. The pH is then adjusted with the citric acid and, if necessary, the viscosity is adjusted with sodium chloride or other viscosifiers.

The alkylpolyglycoside surfactant of the present invention may also be combined with an acyl isethionate surfactant, thereby providing good foaming or lathering and mildness to end uses where isethionate surfactants find utility. The isethionates find particular utility in soap bars. A typical soap bar will contain (a) from about 10 to about 80% by weight of the composition of a soap of a synthetic, or natural fatty, acid containing from about 8 to about 18 carbon atoms;

(b) from about 10 to about 80% by weight of the composition of a $C_8$–$C_{18}$ fatty acyl isethionate as a non-soap surfactant;

(c) water; and optionally (d) adjuvants, such as pigments, perfumes, electrolytes and the like.

The alkylpolyglycoside surfactants of the present invention, i.e. the Polyglycoside, will be employed in combination with the isethionate and will result in less isethionate being necessary, but retaining, if not improving, lathering efficacy and providing mildness and non-irritation properties. The isethionate and alkylpolyglycoside are then co-surfactants and will be employed in the surfactant component in a weight ratio of alkylpolyglycoside to isethionate of about 10:1 to about 1:10, preferably about 5:1 to about 1:5.

As earlier indicated, the alkylpolyglycoside surfactant compositions of the present invention are useful in toothpaste, mouthwash and antiperspirant compositions. A typical toothpaste composition will contain from about 0.025 to about 2.5% by weight of alkylpolyglycoside. Toothpaste composition may typically also include polishing agents, antimicrobial agents, humectants, consistency regulators, flavoring oils and solubilizers, sweeteners and other optional adjuvants.

Where employed, the polishing agents are typically aluminum silicates, phosphates such as dicalcium phosphate, and α-aluminum oxide trihydrate, Al(OH)$_3$, or weakly, calcined alumina containing about 20% by weight gamma-aluminum oxide and 80% by weight alpha-aluminum oxide. These are commercially available in various degrees of calcination, fineness and apparent density. Typical humectants include glycerol and sorbitol, which are preferred, propylene glycol and polyethylene glycols. Typical water-soluble consistency regulators include the nonionic polysaccharide derivatives such as methyl, hydroxypropyl, hydroxypropylmethyl and hydroxyethyl ethers of cellulose, starch, guar and vegetable gums. Where employed, the antimicrobial agents are typically antimicrobial biguanide compounds such as 1,1'-hexamethylene bis [5-(4-chlorophenyl)-biguanide], known as "chlorhexidine" and 1,1'-hexamethylene bis [5-(4-fluorophenyl)-biguanide], known as "fluorhexidine," employed in the form of a water-soluble, physiologically compatible salt, such as the acetate or glucanate.

EXAMPLE 20

The following are illustrative examples of toothpaste formulations employing the Polyglycoside product of the present invention as earlier described.

| Ingredient | % wt/wt |
|---|---|
| A. | |
| Polyglycoside | 4.0 |
| Magnesium Aluminum Silicate | 1.1 |
| Sodium Carboxymethylcellulose | 0.6 |
| Sorbitol (70% solution) | 10.0 |
| Glycerine | 15.0 |
| Dicalcium Phosphate.2H$_2$O | 46.0 |
| Flavor | 1.0 |
| Preservative | q.s. |
| Water | Balance |
| B. | |
| Polyglycoside | 4.0 |
| Hydroxypropyl Methylcellulose | 1.0 |
| Glycerine | 15.0 |
| Sorbitol (70% solution) | 15.0 |
| Calcium Carbonate | 10.0 |
| Dicalcium Phosphate.2H$_2$O | 40.0 |
| Flavor | 1.0 |
| Preservative | q.s. |
| Water | Balance |

A mouthwash composition will typically contain from about 0.005 to about 1% of alkylpolyglycoside in an aqueous, homogenous composition which may also contain up to about 20% by weight of ethanol. A typical mouthwash composition may also contain antimicrobial agents, flavoring oils and solubilizers, sweeteners and other adjuvants.

EXAMPLE 21

The following is an illustrative example of a mouthwash composition employing the Polyglycoside product of the present invention as earlier described.

| Ingredient | % wt/wt |
|---|---|
| Polyglycoside | 2.0 |
| Water | 80.762 |
| Ethanol | 17.0 |
| Sodium Saccharin | 0.15 |
| Spearmint Oil | 0.04 |
| Menthol | 0.04 |
| Cinnamon Oil | 0.008 |
| Dye | q.s. |

What is claimed is:

1. A hard surface cleaner containing
   (i) an alkylpolyglycoside surfactant composition having an HLB in the range of about 10 to about 16, in which the alkyl group contains from about 6 to about 20 carbon atoms, said alkyl polyglycoside surfactant composition comprising a mixture of:
      (a) an alkylpolyglycoside component having a non-Flory distribution of glycosides containing a degree of polymerization of 2 and higher in progressively decreasing amounts, in which the amount by weight of polyglycoside having a degree of polymerization of 2, or mixtures thereof with a polyglycoside having a degree of polymerization of 3, predominate and having an average degree of polymerization of about 1.8 to about 3; and
      (b) at least one other glycoside component having an average alkyl chain length less than the average alkyl chain length of component (a); and
   wherein the alkylpolyglycoside component (a) is an at least binary component and the glycoside component (b) is an alkylpolyglycoside at least binary component and each of the binary components (a) and (b) is present in the mixture in relation to the average carbon chain length in an amount to provide the alkylpolyglycoside surfactant composition with an average carbon chain length of about 9 to about 14 and an HLB in the range of about 10 to about 16; and
   (ii) at least one hard surface cleaner adjuvant selected from the group consisting of a co-surfactant; a conditioning agent; a hydrotrope; a solvent; a filler; a coloring agent; a dye; a brightening agent; a fragrance; a preservative; a consistency regulator; a polishing agent; and a humectant.

2. A hard surface cleaner as defined in claim 1 in which the average chain length of the alkylpolyglycoside surfactant composition is above 9 and below about 12 and component (a) is a mixture of a $C_{12}$ alkylpolyglycoside, a $C_{14}$alkylpolyglycoside, and a $C_{16}$ alkylpolyglycoside; and component (b) is a binary mixture of a $C_8$ alkylpolyglycoside and a $C_{10}$ alkylpolyglycoside in which the ratio by weight of the $C_8$ and $C_{10}$ alkylpolyglycoside component (b) to the mixture of the $C_{12}$, $C_{14}$, and $C_{16}$ alkylpolyglycoside component (a) is about 1:1 to about 10:1.

3. A hard surface cleaner as defined in claim 2 in which the ratio by weight of the mixture of $C_8$ and $C_{10}$ alkylpolyglycosides to the mixture of $C_{12}$, $C_{14}$ and $C_{16}$ alkylpolyglycosides is above 1.25:1 to about 4:1.

4. A hard surface cleaner as defined in claim 3 in which said ratio is about 2:1.

5. A hard surface cleaner as defined in claim 1 and further comprising an anionic surfactant.

6. A soil cleaning composition containing
   (i) an alkylpolyglycoside surfactant composition having an HLB in the range of about 10 to about 16, in which the alkyl group contains from about 6 to about 20 carbon atoms, said alkyl polyglycoside surfactant composition comprising a mixture of:

(a) an alkylpolyglycoside component having a non-Flory distribution of glycosides containing a degree of polymerization of 2 and higher in progressively decreasing amounts, in which the amount by weight of polyglycoside having a degree of polymerization of 2, or mixtures thereof with a polyglycoside having a degree of polymerization of 3, predominate and having an average degree of polymerization of about 1.8 to about 3, and (b) at least one other glycoside component having an average alkyl chain length less than the average alkyl chain length of component (a); and wherein the alkylpolyglycoside component (a) is an at least binary component and the glycoside component (b) is an alkylpolyglycoside at least binary component and each of the binary components (a) and (b) is present in the mixture in relation to the average carbon chain length in an amount to provide the alkylpolyglycoside surfactant composition with an average carbon chain length of about 9 to about 14 and an HLB in the range of about 10 to about 16; and (ii) at least one soil cleaning adjuvant selected from the group consisting of a co-surfactant; a conditioning agent; a hydrotrope; a solvent; a filler; a coloring agent; a dye; a brightening agent; a fragrance; a preservative; a consistency regulator; a polishing agent; and a humectant.

7. A soil cleaning composition as defined in claim 6 in which the average chain length of the alkylpolyglycoside surfactant composition is above 9 and below about 12 and component (a) is a mixture of a $C_{12}$ alkylpolyglycoside, a $C_{14}$ alkylpolyglycoside, and a $C_{16}$ alkylpolyglycoside; and component (b) is a binary mixture of a $C_8$ alkylpolyglycoside and a $C_{10}$ alkylpolyglycoside in which the ratio by weight of the $C_8$ and $C_{10}$ alkylpolyglycoside component (b) to the $C_{12}$, $C_{14}$, and $C_{16}$ alkylpolyglycoside component (a) is about 1:1 to about 10:1.

8. A soil cleaning composition as defined in claim 7 in which the ratio by weight of the mixture of $C_8$ and $C_{10}$ alkylpolyglycosides to the mixture of $C_{12}$, $C_{14}$ and $C_{16}$ alkylpolyglycosides is about 2:1 to about 3:1.

9. A laundry detergent containing an alkylpolyglycoside surfactant composition having an HLB in the range of about 10 to about 16, in which the alkyl group contains from about 6 to about 20 carbon atoms, said alkyl polyglycoside surfactant composition comprising a mixture of:

(a) an alkylpolyglycoside component having a non-Flory distribution of glycosides containing a degree of polymerization of 2 and higher in progressively decreasing amounts, in which the amount by weight of polyglycoside having a degree of polymerization of 2, or mixtures thereof with a polyglycoside having a degree of polymerization of 3, predominate and having an average degree of polymerization of about 1.8 to about 3; and (b) at least one other glycoside component having an average alkyl chain length less than the average alkyl chain length of component (a); and wherein the alkylpolyglycoside component (a) is an at least binary component and the glycoside component (b) is an alkylpolyglycoside at least binary component and each of the binary components (a) and (b) is present in the mixture in relation to the average carbon chain length in an amount to provide the alkylpolyglycoside surfactant composition with an average carbon chain length of about 9 to about 14 and an HLB in the range of about 10 to about 16; and (ii) at least one laundry detergent adjuvant selected from the group consisting of a co-surfactant; a conditioning agent; a hydrotrope; a solvent; a filler; a coloring agent; a dye; a brightening agent; a fragrance; a preservative; a consistency regulator; a polishing agent; and a humectant.

10. A laundry detergent composition as defined in claim 9 in which the average chain length of the alkylpolyglycoside surfactant composition is above 9 and below about 12 and component (a) is a mixture of a $C_{12}$ alkylpolyglycoside, a $C_{14}$ alkylpolyglycoside, and a $C_{16}$ alkylpolyglycoside; and component (b) is a binary mixture of a $C_8$ alkylpolyglycoside and a $C_{10}$ alkylpolyglycoside in which the ratio by weight of the $C_8$ and $C_{10}$ alkylpolyglycoside component (b) to the mixture of the $C_{12}$, $C_{14}$, and $C_{16}$ alkylpolyglycoside component (a) is about 1:1 to about 10:1.

11. A laundry detergent composition as defined in claim 10 in which the ratio of component (b) to component (a) is above 1.25:1 to about 4:1.

12. A laundry detergent composition as defined in claim 11 in which the ratio of component (b) to (a) is about 2:1 to about 3:1.

13. A method of preparing a cleaning composition comprising adding to said cleaning composition a surfactant effective amount of an alkylpolyglycoside surfactant having an HLB in the range of about 10 to about 16, in which the alkyl group contains from about 6 to about 20 carbon atoms, said alkyl polyglycoside surfactant composition comprising a mixture of:

(a) an alkylpolyglycoside component having a non-Flory distribution of glycosides containing a degree of polymerization of 2 and higher in progressively decreasing amounts, in which the amount by weight of polyglycoside having a degree of polymerization of 2, or mixtures thereof with a polyglycoside having a degree of polymerization of 3, predominate and having an average degree of polymerization of about 1.8 to about 3; and (b) at least one other glycoside component having an average alkyl chain length less than the average alkyl chain length of component (a); and wherein the alkylpolyglycoside component (a) is an at least binary component and the glycoside component (b) is an alkylpolyglycoside at least binary component and each of the binary components (a) and (b) is present in the mixture in relation to the average carbon chain length in an amount to provide the alkylpolyglycoside surfactant composition with an average carbon chain length of about 9 to about 14 and an HLB in the range of about 10 to about 16.

14. A method as defined in claim 13 wherein said cleaning composition is a hard surface cleaner or a laundry detergent composition.

15. An alkyl polyglycoside composition having an HLB in the range of about 10 to about 16, in which the alkyl group contains from about 6 to about 20 carbon atoms, said alkyl polyglycoside surfactant composition comprising a mixture of:

(a) an alkylpolyglycoside component having a non-Flory distribution of glycosides containing a degree of polymerization of 2 and higher in progressively decreasing amounts, in which the amount by weight of polyglycoside having a degree of polymerization of 2, or mixtures thereof with a polyglycoside having a degree of polymerization of 3, predominate and having an average degree of polymerization of about 1.8 to about 3; and (b) at least one other glycoside component having an average alkyl chain length less than the average alkyl chain length of component (a); and wherein the alkylpolyglycoside component (a) is an at least binary component and the glycoside component (b) is an at least binary monoglycoside component.

16. An alkylpolyglycoside composition as defined in claim 15 wherein the alkylpolyglycoside component (a) is a mixture of a $C_{12}$ alkylpolyglycoside, a $C_{14}$ alkylpolyglycoside and a $C_{16}$ alkylpolyglycoside.

17. An alkylpolyglycoside composition as defined in claim 16 in which component (b) is a binary mixture of a $C_8$ and $C_{10}$ monoglycoside.

18. An alkylpolyglycoside composition as defined in claim 17 in which the ratio by weight of (b) to (a) is about 1:1 to about 4:1.

19. A method of preparing an improved alkylpolyglycoside surfactant composition in which the alkyl groups contain from about 6 to about 20 carbon atoms comprising selecting a predetermined average carbon chain length of the alkyl moiety for the composition and mixing two or more of at least binary components of alkylpolyglycosides, each binary component having an average alkyl chain length such that when mixed, the amounts of the binary components mixed are effective to provide the predetermined selected average alkyl moiety and the surfactant properties and wherein at least one, or both binary components, comprise a non-Flory distribution of polyglycosides derived from an acid-catalyzed reaction of an alcohol containing 6–20 carbon atoms and a suitable saccharide from which excess alcohol has been separated.

20. A method as defined in claim 19, in which the predetermined average alkyl moiety chain length is above about 9 and one of the binary components has an average alkyl chain length less than the predetermined selected average alkyl moiety and another binary component has an average alkyl having alkyl chain length higher than the predetermined selected alkyl moiety.

21. A method as defined in claim 20 in which said binary component of alkylpolyglycosides having an average alkyl chain length higher than the predetermined selected alkyl moiety is a mixture of a $C_{12}$ alkylpolyglycoside, a $C_{14}$ alkylpolyglycoside and a $C_{16}$ alkylpolyglycoside.

22. A method as defined in claim 21 in which said binary component of alkylpolyglycosides having an average alkyl chain length less than the predetermined selected alkyl moiety is a mixture of a $C_8$ alkylpolyglycoside and a $C_{10}$ alkylpolyglycoside.

23. A method as defined in claim 22 in which the ratio by weight of the binary component of the $C_8$ and $C_{10}$ alkylpolyglycosides mixture to the binary component of the $C_{12}$, $C_{14}$ and $C_{16}$ alkylpolyglycosides mixture is about 1:1 to about 10:1.

24. A method as defined in claim 23 in which said ratio is above about 1:1 to about 4:1.

25. A method as defined in claim 23 in which said ratio is from about 1.5:1 to about 4:1.

26. A method as defined in claim 23 in which said ratio is about 1.7:1 to about 2:1.

27. A method as defined in claim 23 in which the average alkyl chain length is about 10.3 and the HLB of the composition is about 13.

28. A method as defined in claim 20, wherein said predetermined average alkyl moiety chain length is about 10.

29. A method as defined in claim 20, in which said binary component of alkylpolyglycoside having an average alkyl chain length less than the predetermined selected average alkyl moiety is a mixture of a $C_8$ alkylpolyglycoside and a $C_{10}$ alkylpolyglycoside.

30. A method as defined in claim 19, wherein the average chain length of the alkyl chain in the product resulting from the mixture of the binary components is in the range of about 9 to about 14.

31. A method as defined in claim 30, in which said average chain length is about 9 to about 12.

32. A method as defined in claim 31 in which said improved alkylpolyglycoside surfactant composition has an HLB in the range of about 10 to about 16.

33. A method as defined in claim 32, in which said improved alkylpolyglycoside surfactant composition has an HLB of about 11 to about 14.

* * * * *